(12) United States Patent
Lund et al.

(10) Patent No.: US 12,065,685 B1
(45) Date of Patent: Aug. 20, 2024

(54) UDP-GLYCOSYLTRANSFERASE VARIANTS AND USES THEREOF

(71) Applicant: AMYRIS, INC., Emeryville, CA (US)

(72) Inventors: Sean Lund, Emeryville, CA (US); Gale Wichmann, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 0 days.

(21) Appl. No.: 18/368,369

(22) Filed: Sep. 14, 2023

Related U.S. Application Data

(63) Continuation of application No. 16/871,324, filed on May 11, 2020, now abandoned.

(60) Provisional application No. 62/846,909, filed on May 13, 2019.

(51) Int. Cl.
  *C12P 19/56* (2006.01)
  *C12N 15/81* (2006.01)

(52) U.S. Cl.
  CPC ............. *C12P 19/56* (2013.01); *C12N 15/81* (2013.01); *C12Y 106/02004* (2013.01); *C12Y 114/14* (2013.01); *C12Y 205/01029* (2013.01); *C12Y 402/03019* (2013.01); *C12Y 505/01012* (2013.01)

(58) Field of Classification Search
  None
  See application file for complete search history.

(56) References Cited

U.S. PATENT DOCUMENTS

| | | |
|---|---|---|
| 8,236,512 B1 | 8/2012 | Zhao et al. |
| 8,415,136 B1 | 4/2013 | Gardner et al. |
| 2010/0285549 A1 | 11/2010 | Muramatsu et al. |
| 2011/0281315 A1 | 11/2011 | Muramatsu et al. |
| 2014/0329281 A1 | 11/2014 | Houghton-Larsen et al. |
| 2014/0357588 A1 | 12/2014 | Markosyan et al. |
| 2015/0159188 A1 | 6/2015 | Ono et al. |
| 2017/0332673 A1 | 11/2017 | Philippe et al. |

FOREIGN PATENT DOCUMENTS

| | | |
|---|---|---|
| WO | WO 2013/022989 | 2/2013 |
| WO | WO 2014/193888 | 12/2014 |
| WO | WO 2016/038095 | 3/2016 |
| WO | WO 2016/196321 | 12/2016 |

OTHER PUBLICATIONS

Anderson et al., "Nucleotide Sequence and Expressionin Esherichiacoliofthe 3-Hydroxy-3-Methylglutaryl Coenzyme A Lyase Gene of Pseudomonasmevalonii", Journal of Bacteriology, Dec. 1989, vol. 171, No. 12, pp. 6468-6472.
Beach et al., "Cloning, Sequencing, and Overexpression of mvaA, Which Encodes Pseudomonas mevalonii 3-Hydroxy-3-Methylglutaryl CoenzymeAReductase", Journal of Bacteriology, Jun. 1989, vol. 171, No. 6, pp. 2994-3001.
Bensch et al., "Purification and Properties of 3-Hydroxy-3-methylglutaryl Coenzyme A Reductase from Pseudomonas", The Journal Of Biological Chemistry, vol. 245, No. 15, Aug. 10, 1970, pp. 3755-3762.
Crane et al., "Regulated accumulation of 3-hydroxy-3-methylglutaryl CoA reductase protein in potato cell cultures: effects of calcium and enzyme inhibitors", 2002, J. Plant Physiology, vol. 159, pp. 1301-1307.
Fimognari et al., "Substrate-CompetitiveInhibition of Bacterial Mevalonate: Nicotinamide-Adenine Dinucleotide Oxidoreductase (acylatingCoA)", Biochemistry, Oct. 1965, vol. 4, No. 10, pp. 2086-2090.
Hedl et al., "Class II 3-Hydroxy-3-Methylglutaryl Coenzyme A Reductases", Journal Of Bacteriology, Apr. 2004, vol. 186, No. 7, pp. 1927-1932.
Kim et al., "Dual coenzyme specificity of Archaeoglobus fulgidus HMG-CoA reductase", Protein Science, 2000, vol. 9, pp. 1226-1234.
Kosaric, et al., "Ethanol", Wiley-VCH Verlag Gmbh & Co. KDaA, Weinheim, Germany, 2007, DOI: 10.1002/14356007.a09_587; 76 pages.
Kovalchuk et al., "Phylogenetic analysis of fungal ABC transporters", Kovalchuk and Driessen BMC Genomics, 2010, vol. 11:177; 21 pages.
Okamura et al., "Unprecedented acetoacetyl-coenzyme A synthesizing enzyme of the thiolase superfamily involved in the mevalonate pathway", PNAS, Jun. 22, 2010, vol. 107, No. 25, pp. 11265-11270.
Richman et al., "Functional genomics uncovers three glucosyltransferases involved in the synthesis of the major sweet glucosides of Stevia rebaudiana", The Plant Journal, 2005, vol. 41, pp. 56-67.
Siddiqi et al., "Bacterial Metabolism of Mevalonic Acid Conversion To Acetoacetate", Biochemical and Biophysical Research Communications, 1962, vol. 8, No. 2, pp. 110-113.
Siddiqi et al., "Bacterial Metabolism of Mevalonic Acid", Journal of Bacteriology, Jan. 1967, vol. 93, No. 1, pp. 207-214.
Takatsuji et al., "Studies On Isoprenoid Biosynthesis With Bacterial Intact Cells", Biochemical and Biophysical Research Communications, Jan. 14, 1983, vol. 110, No. 1, pp. 187-193.

(Continued)

*Primary Examiner* — Christian L Fronda
(74) *Attorney, Agent, or Firm* — SQUIRE PATTON BOGGS (US) LLP

(57) ABSTRACT

Provided herein are genetically modified host cells, compositions, and methods for improved production of steviol glycosides. The host cells are genetically modified to contain a heterologous nucleic acid that expresses novel and optimized variants of UGT76G1. The host cell further contains one or more heterologous nucleotide sequence encoding further enzymes of a pathway capable of producing one or more steviol glycosides in the host cell. The host cells, compositions, and methods described herein provide an efficient route for the heterologous production of rebaudioside M.

2 Claims, 14 Drawing Sheets
Specification includes a Sequence Listing.

(56) References Cited

OTHER PUBLICATIONS

Watanabe et al., "Ethanol production from xylose by recombinant *Saccharomyces cerevisiae* expressing proteinengineered NADH-preferring xylose reductase from *Pichia stipites*", 2007, Microbiology, vol. 153, pp. 3044-3054; DOI 10.1099/mic.0.2007/007856-0.
Wilding et al., "Essentiality, Expression, and Characterization of the Class II 3-Hydroxy-3-Methylglutaryl Coenzyme A Reductase of *Staphylococcus aureus*", Journal of Bacteriology, Sep. 2000, vol. 182, No. 18, pp. 5147-5152.
Uni Prot Accession No. A0A0251SL80_H Elan, published Nov. 22, 2017.
Uni Prot Accession No. A0A2P5YL83_GOSBA, published May 23, 2018.
Uni Prot Accession No. A0A059BIAO_EUCGR, published Jul. 9, 2014.
Uni Prot Accession No. V4UFE1_9ROSI, published Jan. 22, 2014.
PIR Accession No. T45605, published Feb. 4, 2000.
Gen Bank Accession No. ACM47734.1, published Feb. 7, 2009.

relative amounts of steviol glycosides produced in strain 2 with combinatorial UGT76G1 mutant alleles versus wt control

UDP-GLYCOSYLTRANSFERASE VARIANTS AND USES THEREOF

CROSS-REFERENCE TO RELATED APPLICATIONS

This application is a continuation of Ser. No. 16/871,324 filed May 11, 2020, which claims benefit of U.S. Provisional Application No. 62/846,909 filed May 13, 2019. The disclosures of the above referenced applications are incorporated by reference herein in their entireties.

SEQUENCE LISTING

The application contains a Sequence Listing which has been submitted electronically in .XML format and is hereby incorporated by reference in its entirety. Said .XML copy, created on Jan. 3, 2024, is named "AM-9800 C1.xml" and is 26,747 bytes in size. The sequence listing contained in this .XML file is part of the specification and is hereby incorporated by reference herein in its entirety.

FIELD OF THE INVENTION

The present disclosure relates to UDP-glycosyltransferase (UGT76G1) variants, host cells comprising the same, and methods of their use for the production of heterologous molecules.

BACKGROUND

Reduced-calorie sweeteners derived from natural sources are desired to limit the health effects of high-sugar consumption. The *stevia* plant (*Stevia rebaudiana* Bertoni) produces a variety of sweet-tasting glycosylated diterpenes termed steviol glycosides. Of all the known steviol glycosides, Reb M has the highest potency (~300 times sweeter than sucrose) and has the most appealing flavor profile. However, Reb M is only produced in minute quantities by the *stevia* plant and is a small fraction of the total steviol glycoside content (<1.0%), making the isolation of Reb M from *stevia* leaves impractical. Alternative methods of obtaining Reb M are needed. One such approach is the application of synthetic biology to design microorganisms (e.g. yeast) that produce large quantities of Reb M from sustainable feedstock sources.

To economically produce a product using synthetic biology, each step in the bioconversion from feedstock to product needs to have a high conversion efficiency (ideally >90%). In our engineering of yeast to produce Reb M, we noted that particular enzymatic steps performed poorly in yeast when the wild-type enzyme was used. In order to increase the productivity and yield of Reb M in microorganisms we sought to produce variant enzymes that performed better than wild-type enzymes. One such enzyme is the UDP-glycosyltransferase enzyme UGT76G1 which catalyzes the conversion of Reb D to Reb M.

SUMMARY OF THE INVENTION

Provided herein are compositions and methods for the improved conversion of Reb D to Reb M. These compositions and methods are based in part on the production of certain variant UGT76G1 enzymes that are capable of converting Reb D to Reb M with high efficiency.

In one aspect the invention provides a variant UDP-glycosyltransferase polypeptide having the amino acid sequence of SEQ ID NO: 1, wherein the sequence further has one or more amino acid substitutions. In an embodiment of the invention the one or more amino acid substitutions are selected from (L85H); (L200G); (L379Q); (H155I); (H155V); (L200K); (V20G); (L200C); (A125F); (H155G); (H155T); (H155L); (L200E); (L200M); and (L379M).

In another aspect the invention provides for a variant UDP-glycosyltransferase polypeptide comprising the amino acid sequence of SEQ ID NO:1, wherein the sequence further comprises two or more amino acid substitutions. In a preferred embodiment of the invention the two or more amino acid substitutions are selection from (A125F); (H155G); (H155T); (H155L); (L200E); (L200M); (L379M); (H155V, L200M); (H155G, L200E), (L85H, A125F, H155G, L200M); (A125F, H155G, L200K, L379M); (L200K, L379Q); (A125F, H155T, L200M); (L85H, L200M, L379Q); (L85H, H155G, L200G, L379M); (L85H, A125F, H155V, L200M); (L85H, A125F, H155I, L200C, L379Q); (A125F, H155L, L200E, L379Q); (H155T, L200G, L379M); (H155L, L200M); (H155V, L200C); (L85H, H155T, L200G); (L85H, H155I, L200C, L379Q); (H155I, L200M, L379Q); (L85H, A125F, H155T, L200E, L379M); (L85H, H155T, L200M); (H155V, L200C, L379M); (L85H, A125F, L200M, L379M); (H155V, L379Q); (L85H, L200K, L379M); (L85H, A125F, H155L, L200M, L379Q); (L85H, A125F, H155I, L200K, L379M); (H155I, L379M); (L200M, L379M); (L85H, H155V, L200G, L379Q); (H155T, L200E); (H155V, L379M); (A125F, H155I, L379M); (H155V, L200C, L379Q); (L85H, H155G, L200K, L379Q); (A125F, H155G, L200M, L379M); (H155T, L200E, L379Q); (L200K, L379G); (L85H, H155L, L200C, L379M); (A125F, H155I, L200K, L379M); (L85H, H155V, L200M); (L85H, H155V, L200E, L379V); (L85H, H155V, L200M, L379Q); (L85H, L200M, L379M); (H155V, L200E, L379M); (L85H, H155I, L200M, L379M); (L85H, H155I, L200M, L379Q); (L85H, A125F, H155T, L200C, L379M); (L85H, A125F, H155L, L200K, L379M); (V20L, L85M, A125P); (L85H, H155L, L200K, L379M); (L85H, H155V, L200C, L379Q); (H155I, L200K, L379M); (L85H, H155L, L200C); (L85H, A125F, H155L, L379M); (L85H, H155I, L200E, L379M); (L85H, A125F, H155G, L200M, L379M); (L85H, H155L, L200E, L379M); (H155L, L200C); (L85H, H155L, L200C, L379E); (L85H, H155V, L200K, L379Q); (H155T, L200K, L379M); (H155V, L200G, L379M); (L85H, A125F, H155V, L200M, L379M); (A125F, H155G, L200C, L379M); (A125F, H155L, L379M); (L85H, H155L, L200G, L379M); (L85H, H155L, L200E, L379Q); (H155G, L200E, L379M); (H155L, L200C, L379Q); (L85H, H155V, L379M); (L85H, A125F, H155I, L200C, L379M); (H155G, L200C, L379M); (A125F, H155V, L200M, L379M); and (H155L, L200E).

In another embodiment the invention provides nucleic acids encoding the variant UGT76G1. In a further embodiment the invention provides a host cell comprising the polypeptide or the nucleic acid of the invention. In an additional embodiment the host cell is capable of producing one or more steviol glycosides. In yet another embodiment the one or more steviol glycosides are selected from RebA, RebB, RebD, RebE, and RebM. In a preferred embodiment the one or more steviol glycosides is RebM.

In a further aspect of the invention the host cells of the invention contain one or more nucleic acids encoding one or more enzymes of a pathway for making a steviol glycoside. In an embodiment the nucleic acid encodes geranylgeranyl diphosphate synthase. In another embodiment the nucleic acid encodes a copalyl diphosphate synthase. In further embodiments the nucleic acid encodes an ent-kaurene synthase. In yet another embodiment the nucleic acid encodes a kaurenoic acid 13-hydroxylase. In an embodiment the nucleic acid encodes a kaurene oxidase. In further embodiments the nucleic acid encodes a cytochrome P450 reductase. In yet another embodiment the nucleic acid encodes one or more uridine 5'-diphosphate-dependent glycosyltransferases. In a preferred embodiment the host cell contains nucleic acids encoding a geranylgeranyl diphosphate synthase, a copalyl diphosphate synthase, an ent-kaurene synthase, a kaurenoic acid 13-hydroxylase, a kaurene oxidase, a cytochrome P450 reductase, a UGT40087, UGT74G1, UGT85C2, EUGT11, and UGT91D. In an embodiment the host cell is selected from a bacterial cell, a yeast cell, an algal cell, an insect cell, and a plant cell. In another embodiment the host cell is a yeast cell. In a preferred embodiment the host cell is a *Saccharomyces cerevisiae*.

In a further aspect the invention provides for a method for producing one or more steviol glycosides involving culturing a population of host cell of claim 18 in a medium with a carbon source under conditions suitable for making one or more steviol glycosides to yield a culture broth; and recovering the one or more steviol glycosides from the culture broth. In a preferred embodiment the method produces Reb M.

In yet another aspect the invention provides a fermentation composition containing a host cell of the invention; and one or more steviol glycosides produced by the host cell. In a preferred embodiment of the fermentation composition invention the steviol glycoside produced by the host cell is Reb M.

The invention also provides for compositions containing Reb M produced using the variant enzymes of the invention.

DETAILED DESCRIPTION OF THE EMBODIMENTS

Figure 1:
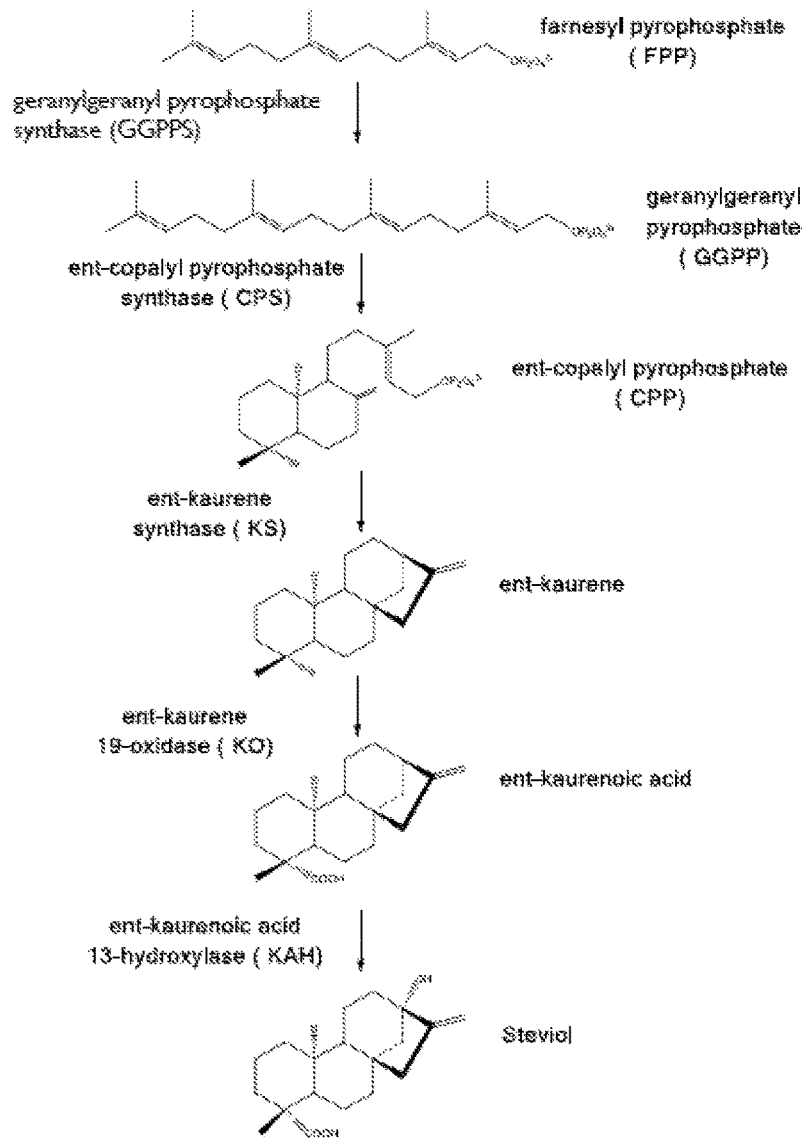
FIG. 1 is a diagram of the biochemical pathway from farnesyl pyrophosphate (FPP) to steviol.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

As used herein, the terms "native" or "endogenous" as used herein with reference to molecules, and in particular polypeptides and polynucleotides, indicates molecules that are expressed in the organism in which they originated or are found in nature. It is understood that expression of native polypeptides or polynucleotides may be modified in recombinant organisms.

As used herein, the term "variant" refers to molecules, and in particular polypeptides and polynucleotides, that differ from a specifically recited "reference" molecule in either structure or sequence. In preferred embodiments the reference is a wild-type molecule. With respect to polypeptides and polynucleotides, variants refer to substitutions, additions, or deletions of the amino acid or nucleotide sequences respectively.

As used herein, the term "heterologous nucleic acid expression cassette" refers to a nucleic acid sequence that comprises a coding sequence operably linked to one or more regulatory elements sufficient to express the coding sequence in a host cell.

As used herein, the term "parent cell" refers to a cell that has an identical genetic background as a genetically modified host cell disclosed herein except that it does not comprise one or more particular genetic modifications engineered into the modified host cell, for example, one or more modifications selected from the group consisting of: heterologous expression of an enzyme of a steviol pathway, steviol glycoside pathway, heterologous expression of an enzyme of a steviol glycoside pathway, heterologous expression of a geranylgeranyl diphosphate synthase, heterologous expression of a copalyl diphosphate synthase, heterologous expression of a kaurene synthase, heterologous expression of a kaurene oxidase, heterologous expression of a steviol synthase (kaurenoic acid hydroxylase), heterologous expression of a cytochrome P450 reductase, heterologous expression of a UDP-glycosyltransferase including for example EUGT11, UGT74G1, UGT85C2, UGT91D, and UGT40087 or variants thereof.

As used therein, the terms "ABC-transporter" and "ATP Binding Cassette Transporter" refer to a super-family of membrane associated polypeptides that couple adenosine triphosphate (ATP) hydrolysis to the translocation of various substrates across biological membranes.

As used herein, the term "medium" refers to culture medium and/or fermentation medium.

As used herein, the term "fermentation composition" refers to a composition which comprises genetically modified host cells and products or metabolites produced by the genetically modified host cells. An example of a fermentation composition is a whole cell broth, which may be the entire contents of a vessel, including cells, aqueous phase, and compounds produced from the genetically modified host cells.

As used herein, the term "production" generally refers to an amount of steviol glycoside produced by a genetically modified host cell provided herein. In some embodiments, production is expressed as a yield of steviol glycoside by the host cell. In other embodiments, production is expressed as the productivity of the host cell in producing the steviol glycoside.

As used herein, the term "yield" refers to production of a steviol glycoside by a host cell, expressed as the amount of steviol glycoside produced per amount of carbon source consumed by the host cell, by weight.

As used herein, the term "productivity" refers to production of steviol glycoside by a host cell, expressed as the amount of steviol glycoside produced (by weight) per amount of fermentation broth in which the host cell is cultured (by volume) over time (per hour).

As used herein, the term "kaurenoic acid" refers to the compound kaurenoic acid, including any stereoisomer of kaurenoic acid. In preferred embodiments, the term refers to the enantiomer known in the art as ent-kaurenoic acid and having the following structure:

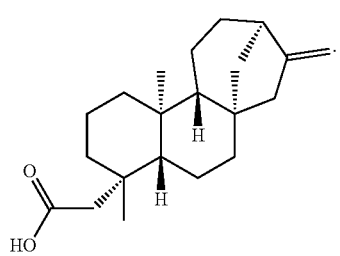

As used herein, the term "steviol" refers to the compound steviol, including any stereoisomer of steviol. In preferred embodiments, the term refers to the compound having the following structure:

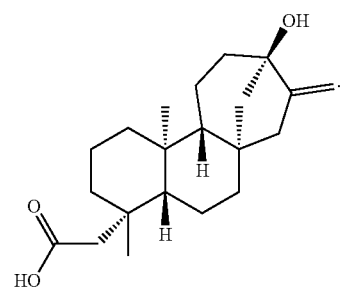

As used herein, the term "steviol glycoside" refers to a glycoside of steviol including but not limited to 19-glycoside, steviolmonoside, steviolbioside, rubusoside, dulcoside B, dulcoside A, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, rebaudioside D2, and rebaudioside M2.

As used herein, the term "rebaudioside M" or "Reb M" refers to a steviol glycoside having the following structure:

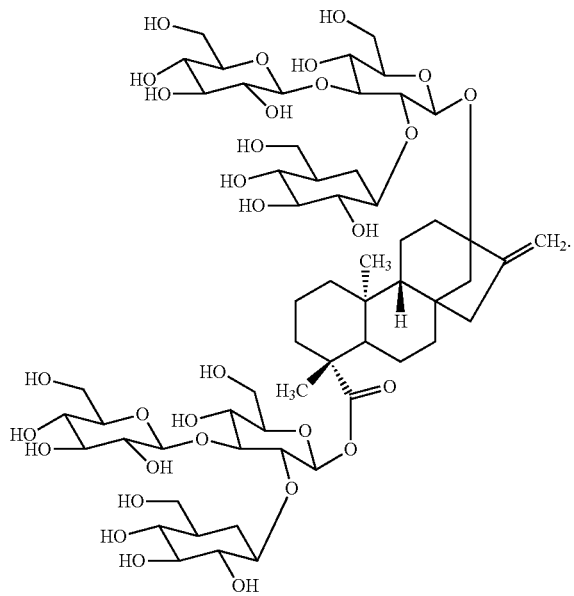

As used herein, the term "sequence identity" or "percent identity" in the context of two or more polynucleotide or polypeptide sequences, refers to two or more sequences or subsequences that are the same or have a specified percentage of nucleotides or amino acid residues that are the same. For example, the sequence may have a percent identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer programs and mathematical algorithms known in the art. Such algorithms that calculate percent sequence identity generally account for sequence gaps and mismatches over the comparison region. Programs that compare and align sequences, like Clustal W (Thompson et al. (1994) *Nuclei Acids Res.*, vol. 22, pp. 4673-4680), ALIGN (Myers et al., (1988) *CABIOS*, vol. 4, pp. 11-17), FASTA (Pearson et al., (1988) *PNAS*, vol. 85, pp. 2444-2448; Pearson (1990) *Methods Enzymol.*, vol. 183, pp. 63-98), and gapped BLAST (Altschul et al., (1997) *Nucleic Acids Res.*, vol. 25, pp. 3389-3402) are useful for this purpose. The BLAST or BLAST 2.0 (Altschul et al., (1990) *J. Mol. Biol.*, vol. 215 pp. 403-410) are available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=2, Nucleic mismatch=−3, Expectation value=10.0, Word size=11, Max matches in a query range=0). For polypeptide sequence alignment and sequence and sequence identity calculations, BLASTP program is used with its default parameters (Alignment matrix=BLOSUM62; Gap costs: Existence=11, Extension=1; Compositional adjustments=Conditional compositional score, matrix adjustment; Expectation value=10.0; Word size=6; Max matches in a query range=0). Alternatively, the following program and parameters can be used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix. In the embodiments described herein, the sequence identity is calculated using BLASTN or BLASTP programs using their default parameters. In the embodiments described herein, the sequence alignment of two or more sequences are performed using Clustal W using the suggested default parameters (Dealign input sequences: no; Mbed-like clustering guide-tree: yes; Mbed-like clustering iteration: yes; number of combined iterations: default(0); Max guide tree iterations: default; Max HMM iterations: default; Order: input)

In further embodiments, the host cells further comprise one or more enzymes capable of making geranylgeranyl diphosphate from a carbon source. These include enzymes of the DXP pathway and enzymes of the MEV pathway. Useful enzymes and nucleic acids encoding the enzymes are known to those of skill in the art. Exemplary enzymes of each pathway are described below and further described, for example, in US2016/0177341 A1 which is incorporated by reference herein in its entirety.

In some embodiments, the host cells comprise one or more or all of the isoprenoid pathway enzymes selected from the group consisting of: (a) an enzyme that condenses two molecules of acetyl-coenzyme A to form acetoacetyl-CoA (e.g., an acetyl-coA thiolase); (b) an enzyme that condenses acetoacetyl-CoA with another molecule of acetyl-CoA to form 3-hydroxy-3-methylglutaryl-CoA (HMG-CoA) (e.g., an HMG-CoA synthase); (c) an enzyme that converts HMG-CoA into mevalonate (e.g., an HMG-CoA reductase); (d) an enzyme that converts mevalonate into mevalonate 5-phosphate (e.g., a mevalonate kinase); (e) an enzyme that converts mevalonate 5-phosphate into mevalonate 5-pyrophosphate (e.g., a phosphomevalonate kinase); (f) an enzyme that converts mevalonate 5-pyrophosphate into isopentenyl diphosphate (IPP) (e.g., a mevalonate pyrophosphate decarboxylase); (g) an enzyme that converts IPP into dimethylallyl pyrophosphate (DMAPP) (e.g., an IPP isomerase); (h) a polyprenyl synthase that can condense IPP and/or DMAPP molecules to form polyprenyl compounds containing more than five carbons; (i) an enzyme that condenses IPP with DMAPP to form geranyl pyrophosphate (GPP) (e.g., a GPP synthase); (j) an enzyme that condenses two molecules of IPP with one molecule of DMAPP (e.g., an FPP synthase); (k) an enzyme that condenses IPP with GPP to form farnesyl pyrophosphate (FPP) (e.g., an FPP synthase); (l) an enzyme that condenses IPP and DMAPP to form geranylgeranyl pyrophosphate (GGPP); and (m) an enzyme that condenses IPP and FPP to form GGPP.

In certain embodiments, the additional enzymes are native. In advantageous embodiments, the additional enzymes are heterologous. In certain embodiments, two or more enzymes may be combined in one polypeptide.

Cell Strains

Host cells of the invention provided herein include archae, prokaryotic, and eukaryotic cells.

Suitable prokaryotic host cells include, but are not limited to, any of a gram-positive, gran-negative, and gram-variable bacteria. Examples include, but are not limited to, cells belonging to the genera: *Agrobacterium, Alicyclobacillus, Anabaena, Anacystis, Arhrobacter, Azobacter, Bacillus, Brevibacterium, Chromatium, Clostridium, Corynebacterium, Enterobacter, Envinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus*, and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In a particular embodiment, the host cell is an *Escherichia coli* cell.

Suitable archae hosts include, but are not limited to, cells belonging to the genera: *Aeropyrum, Archaeglobus, Halobacterium, Methanococcus, Methanobacterium, Pyrococcus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malasserzia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastoporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma.*

In some embodiments, the host microbe is *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans,* or *Hansenula polymorpha* (now known as *Pichia angusta*). In some embodiments, the host microbe is a strain of the genus *Candida,* such as *Candida hpolytica, Candida guilliermondii, Candida krusei, Candida pseudotropicalis,* or *Candida utils.*

In preferred embodiments, the host microbe is *Saccharomyces cerevisiae.* In some embodiments, the host is a strain of *Saccharomyces cerevisiae* selected from Baker's yeast, CEN.PK2, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1 BR-1, BR-2, ME-2, VR-2, MA-3, MA-4, CAT-1, CB-1, NR-1, BT-1, and AL-1. In some embodiments, the host microbe is a strain of *Saccharomyces cerevisiae* selected from PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

The Steviol Glycoside Biosynthesis Pathway

In some embodiments, a steviol glycoside biosynthesis pathway is activated in the genetically modified host cells by engineering the cells to express polynucleotides encoding enzymes capable of catalyzing the biosynthesis of steviol glycosides.

In some embodiments, the genetically modified host cells contain a heterologous polynucleotide encoding geranylgeranyl diphosphate synthase (GGPPS), a heterologous polynucleotide encoding copalyl diphosphate synthase (CDPS), a heterologous polynucleotide encoding kaurene synthase (KS), a heterologous polynucleotide encoding kaurene oxidase (KO), a heterologous polynucleotide encoding kaurene acid hydroxylase (KAH), a heterologous polynucleotide encoding cytochrome P450 reductase (CPR), a heterologous polynucleotide encoding a UDP-glucose transferase, a heterologous polynucleotide encoding UGT74G1, a heterologous polynucleotide encoding UGT76G1, a heterologous polynucleotide encoding UGT85C2, a heterologous polynucleotide encoding UGT91D, a heterologous polynucleotide encoding EUGT11, or a heterologous polynucleotide encoding UGT40087. In some embodiments, the genetically modified host cells contain a heterologous polynucleotide encoding a variant GGPPS, CDPS, KS, KO, KAH, CPR, UDP-glucose transferase, UGT74G1, UGT76G1, UGT85C2, UGT91D, EUGT11, or UGT40087. In certain embodiments, the variant enzyme may have from 1 up to 20 amino acid substitutions relative to a reference enzyme. In certain embodiments, the coding sequence of the polynucleotide is codon optimized for the particular host cell.

Geranylgeranyl Diphosphate Synthase (GGPPS)

Geranylgeranyl diphosphate synthases (EC 2.5.1.29) catalyze the conversion of farnesyl pyrophosphate into geranylgeranyl diphosphate. Examples of geranylgeranyl diphosphate synthase include those of *Stevia rebaudiana* (accession no. ABD92926), *Gibberella fujikuroi* (accession no. CAA75568), *Mus musculus* (accession no. AAH69913), *Thalassiosira pseudonana* (accession no. XP_002288339), *Streptomyces clavuligerus* (accession no. ZP-05004570), *Sulfulobus acidocaldarius* (accession no. BAA43200), *Synechococcus* sp. (accession no. ABC98596), *Arabidopsis thaliana* (accession no. MP_195399), and *Blakeslea trispora* (accession no. AFC92798.1), and those described in US2014/0329281 A1.

Copalyl Diphosphate Synthase (CDPS)

Copalyl diphosphate synthases (EC 5.5.1.13) catalyze the conversion of geranylgeranyl diphosphate into copalyl diphosphate. Examples of copalyl diphosphate synthases include those from *Stevia rebaudiana* (accession no. AAB87091), *Streptomyces clavuligerus* (accession no. EDY51667), *Bradyrhizobioum japonicum* (accession no. AAC28895.1), *Zea mays* (accession no. AY562490), *Arabidopsis thaliana* (accession no. NM_116512), and *Oryza sativa* (accession no. Q5MQ85.1), and those described in US2014/0329281 A1.

Kaurene Synthase (KS)

Kaurene synthases (EC 4.2.3.19) catalyze the conversion of copalyl diphosphate into kaurene and diphosphate. Examples of enzymes include those of *Bradyrhizobium japonicum* (accession no. AAC28895.1), *Arabidopsis thaliana* (accession no. Q9SAK2), and *Picea glauca* (accession no. ADB55711.1), and those described in US2014/0329281 A1.

Bifunctional Copalyl Diphosphate Synthase (CDPS) and Kaurene Synthase (KS)

CDPS-KS bifunctional enzymes (EC 5.5.1.13 and EC 4.2.3.19) may also be used in the host cells of the invention. Examples include those of *Phomopsis amygdali* (accession no. BAG30962), *Phaeosphaeria* sp. (accession no. 013284), *Physcomitrella patens* (accession no. BAF61135), and *Gibberella fujikuroi* (accession no. Q9UVY5.1), and those described in US2014/032928 A1, US2014/0357588 A1, US2015/0159188, and WO2016/038095.

Ent-Kaurene Oxidase (KO)

Ent-kaurene oxidases (EC 1.14.13.88) also referred to as kaurene oxidases herein catalyze the conversion of kaurene into kaurenoic acid. Illustrative examples of enzymes include those of *Oryza sativa* (accession no. Q5Z5R4), *Gibberella fujikuroi* (accession no. 094142), *Arabidopsis thaliana* (accession no. Q93ZB2), *Stevia rebaudiana* (accession no. AAQ63464.1), and *Pisum sativum* (Uniprot no. Q6XAF4), and those described in US2014/0329281 A1, US2014/0357588 A1, US2015/0159188, and WO2016/038095.

Kaurenoic Acid Hydroxylase (KAH)

Kaurenoic acid hydroxylases (EC 1.14.13) also referred to as steviol synthases catalyze the conversion of kaurenoic acid into steviol. Examples of enzymes include those of *Stevia rebaudiana* (accession no. ACD93722), *Arabidopsis thaliana* (accession no. NP 197872), *Vitis vinifera* (accession no. XP_002282091), and *Medicago trunculata* (accession no. ABC59076), and those described in US2014/0329281, US2014/0357588, US2015/0159188, and WO2016/038095.

Cytochrome P450 Reductase (CPR)

Cytochrome P450 reductases (EC 1.6.2.4) are necessary for the activity of KO and/or KAH above. Examples of enzymes include those of *Stevia rebaudiana* (accession no. ABB88839), *Arabidopsis thaliana* (accession no. NP 194183), *Gibberella fujikuroi* (accession no. CAE09055), and *Artemisia annua* (accession no. ABC47946.1), and those described in US2014/0329281, US2014/0357588, US2015/0159188, and WO2016/038095.

UDP Glycosyltransferase 74G1 (UGT74G1)

UGT74G1 is capable of functioning as a uridine 5'-diphospho glucosyl: steviol 19-COOH transferase and as a uridine 5'-diphospho glucosyl: steviol-13-O-glucoside 19-COOH transferase. Accordingly, UGT74G1 is capable of converting steviol to 19-glycoside; converting steviol to 19-glycoside, steviolmonoside to rubusoside; and steviolbioside to stevioside. UGT74G1 has been described in Richman et al., 2005, *Plant J*., vol. 41, pp. 56-67; US2014/0329281; WO2016/038095; and accession no. AAR06920.1.

UDP Glycosyltransferase 76G1 (UGT76G1)

UGT76G1 is capable of transferring a glucose moiety to the C-3' position of a acceptor molecule a steviol glycoside (where glycoside=Glcb(1→2)Glc). This chemistry can occur at either the C-13-O-linked glucose of the acceptor molecule, or the C-19-O-linked glucose acceptor molecule. Accordingly, UGT76G1 is capable of functioning as a uridine 5'-diphospho glucosyltransferase to the: (1)C-3' position of the 13-O-linked glucose on steviolbioside in a beta linkage forming Reb B, (2)C-3' position of the 19-O-linked glucose on stevioside in a beta linkage forming Reb A, and (3)C-3' position of the 19-O-linked glucose on Reb D in a beta linkage forming Reb M. UGT76G1 has been described in Richman et al., 2005, Plant J., vol. 41, pp. 56-67; US2014/0329281; WO2016/038095; and accession no. AAR06912.1.

UDP Glycosyltransferase 85C2 (UGT85C2)

UGT85C2 is capable of functioning as a uridine 5'-diphospho glucosyl:steviol 13-OH transferase, and a uridine 5'-diphospho glucosyl: steviol-19-O-glucoside 13-OH transferase. UGT85C2 is capable of converting steviol to steviolmonoside and is also capable of converting 19-glycoside to rubusoside. Examples of UGT85C2 enzymes include those of *Stevia rebaudiana*: see e.g., Richman et al., (2005), Plant J., vol. 41, pp. 56-67; US2014/0329281; WO2016/038095; and accession no. AAR06916.1.

UDP Glycosyltransferase 91D (UGT91D)

UGT91D is capable of functioning as a uridine 5'-diphosphoglucosyl:steviol-13-O-glucoside transferase, transferring a glucose moiety to the C-2' of the 13-O-glucose of the acceptor molecule, steviol-13-O-glucoside (steviolmonoside) to produce steviolbioside. A UGT91D is also capable of functioning as a uridine 5'-diphosphoglucosyl:rubusoside transferase, transferring a glucose moiety to the C-2' of the 13-O-glucose of the acceptor molecule, rubusoside, to provide stevioside. UGT91D is also referred to as UGT91D2, UGT91D2e, or UGT91D-like 3. Examples of UGT91D enzymes include those of *Stevia rebaudiana*: see e.g., accession no. ACE87855.1; US2014/0329281; and WO2016/038095.

UDP Glycosyltransferase 40087 (UGT40087)

UGT40087 is capable of transferring a glucose moiety to the C-2' position of the 19-O-glucose of Reb A to produce Reb D. UGT40087 is also capable of transferring a glucose moiety to the C-2' position of the 19-O-glucose of stevioside to produce Reb E. Examples of UGT40087 include those of accession no. XP_004982059.1 and WO2018/031955.

Additional Uridine Diphosphate-Dependent Glycosyl Transferases Capable of Converting Reb A to Reb D (UGTAD)

In addition to UGT40087, other UGTAD are capable of transferring a glucose moiety to the C-2' position of 19-O-glucose of Reb A to produce Reb D. UGTAD is also capable of transferring a glucose moiety to the C-2' position of 19-O-glucose of stevioside to produce Reb E. Examples of UGTAD include Os_UGT_91C1 from *Oryza sativa* (also referred to as EUGT11 (see WO2013/022989 and accession number XP_01529141.1)); S1_UGT_101249881 from *Solanum lycopersicum* (also referred to as UGTSL2 (see WO2014/193888 and accession no. XP_0042504851)); sr.UGT_925778; Bd_UGT0840 (see accession no. XP_003560669.1); Hv_UGT_V1 (see accession no. BAJ94055.1); Bd_UGT10850 (see accession no. XP_010230871.1); and OB_UGT91B1_like (see accession no. XP_00665045514

ABC-Transporter, Nucleic Acids, Expression Cassettes, and Host Cells

In one aspect, provided herein are recombinant nucleic acids which express ABC-transporters. ABC-transporters of the invention can be identified by sequence-based searches against the sequences of known ABC-transporters. An exemplary sequence database of known ABC-transporters is provided by (Kovalchuk and Driessen, Phylogenetic Analysis of Fungal ABC Transporters, *BMC Genomics*, 2010, 11:177). ABC-transporter BLAST databases may also be generated from additional organisms. In preferred embodiments, fungal sequence databases from (1) *Hansenula polymorpha* DL-1 (NRRL-Y-7560), (2) *Yarrowia lipolytica* ATCC 18945, (3) *Arxula adeninivorans* ATCC 76597, (4) *S. cerevisiae* CAT-1, (5) *Lipomyces starkeyi* ATCC 58690, (6)*Kluyveromyces marxianus*, (7) *Kluyveromyces marxianus* DMKU3-1042, (8) *Komagataella phaffii* NRRL Y-11430, (9) *S. cerevisiae* MBG3370, (10) *S. cerevisiae* MBG3373, (11) *K. lactis* ATCC 8585, (12) *Candida utilis* ATCC 22023, (13) *Pichia pastoris* ATCC 28485, and (14) *Aspergillus oryzae* NRRL5590 serve as sources of ABC-transporters of the invention.

Nucleotide ORF sequences generated from de novo genomic sequencing, assembly, and annotation of various organisms are analyzed by the tblastn algorithm using Biopython or any other suitable sequence analysis software. The tblastn algorithm provides alignments of protein sequences of known ABC-transporters with translated DNA of the nucleotide ORF sequences for each organism in all 6 possible reading frames using BLAST. Exemplary BLAST parameters are standard with evalue=1e-25 (Tables 4 and 5). Hits can be subsequently filtered to ensure a global alignment of at least 2000 nucleotides.

In other embodiments of the invention, the entire proteome of an organism can be pulled from Uniprot using the Uniprot API in order to create a database for a BLAST search. The blastp algorithm can be applied to the Uniprot derived database. In one embodiment, BLAST parameters can be standard, with evalue=0.001. In particular embodiments, filtering can be performed based on a percent identity cutoff of ≥40%, and a percent aligned length cutoff of ≥60%. In preferred embodiments, hits have to match at least one of the 610 seed sequences from the reference.

Once nucleotide sequences are identified, primers can be designed to amplify each complete ORF amplified via PCR. Each PCR primer should ideally have flanking homology to the promoter and terminator DNA sequences of a promoter and terminator used in a heterologous nucleotide expression cassette added to the ends to facilitate homologous recombination of the amplified gene into a landing pad target site to produce the specific ABC-transporter expression cassette. Each ABC-transporter gene can be transformed individually as a single copy into the parental Reb M yeast strain described herein and screened for the ability to increase product titers when overexpressed in vivo.

Preferred ABC-transporters include BPT1 (SEQ ID NO: 15) and CJY1 (SEQ ID NO: 16). These transporters sequester steviol glycoside end products into the extracellular space or the vacuole of the cell and thereby reduce product inhibition of the steviol glycoside enzymes.

Also provided herein are host cells comprising one or more of the ABC-transporter polypeptides or nucleic acids provided herein that are capable of producing steviol glycosides. In certain embodiments, the host cells can produce steviol glycosides from a carbon source in a culture medium. In particular embodiments, the host cells can produce steviol from a carbon source in a culture medium and can further produce Reb A or Reb D from the steviol. In particular embodiments, the host cells can further produce Reb M from the Reb D. In particular embodiments, the Reb D and/or Reb M is transported to the lumen of one or more organelles. In particular embodiments, the Reb D and/or Reb M is transported to the extracellular space (i.e., supernatant).

In certain embodiments, host cells expressing ABC-transporters according to the above embodiments produce at least 20%, at least 30%, at least 40%, at least 50%, at least 60%, at least 70%, at least 80%, at least 90%, or at least 100% more total steviol glycoside (TSG) compared to the parent host cell lacking the ABC-transporter expression cassette.

In certain embodiments, host cells expressing ABC-transporters according to the above embodiments produce at least 20%, at least 30%, at least 40%, at least 50%, at least 60%, at least 70%, or at least 75% more TSG in the supernatant compared to the parent host cell lacking the ABC-transporter expression cassette. In a particular embodiment, host cells expressing ABC-transporters according to the above embodiments produce at least 2-fold, at least 3-fold, at least 4-fold, or at least 5-fold more TSG in the supernatant compared to the parent host cell lacking the ABC-transporter expression cassette.

MEV Pathway FPP and/or GGPP Production

In some embodiments, a genetically modified host cell provided herein comprises one or more heterologous enzymes of the MEV pathway, useful for the formation of FPP and/or GGPP. The one or more enzymes of the MEV pathway may include an enzyme that condenses acetyl-CoA with malonyl-CoA to form acetoacetyl-CoA; an enzyme that condenses two molecules of acetyl-CoA to form acetoacetyl-CoA; an enzyme that condenses acetoacetyl-CoA with acetyl-CoA to form HMG-CoA; or an enzyme that converts HMG-CoA to mevalonate. In addition, the genetically modified host cells may include a MEV pathway enzyme that phosphorylates mevalonate to mevalonate 5-phosphate; a MEV pathway enzyme that converts mevalonate 5-phosphate to mevalonate 5-pyrophosphate; a MEV pathway enzyme that converts mevalonate 5-pyrophosphate to isopentenyl pyrophosphate; or a MEV pathway enzyme that converts isopentenyl pyrophosphate to dimethylallyl diphosphate. In particular, the one or more enzymes of the MEV pathway are selected from acetyl-CoA thiolase, acetoacetyl-CoA synthetase, HMG-CoA synthase, HMG-CoA reductase, mevalonate kinase, phosphomevalonate kinase, mevalonate pyrophosphate decarboxylase, and isopentyl diphosphate:dimethylallyl diphosphate isomerase (IDI or IPP isomerase). The genetically modified host cell of the invention may express one or more of the heterologous enzymes of the MEV from one or more heterologous nucleotide sequences comprising the coding sequence of the one or more MEV pathway enzymes.

In some embodiments, the genetically modified host cell comprises a heterologous nucleic acid encoding an enzyme that can convert isopentenyl pyrophosphate (IPP) into dimethylallyl pyrophosphate (DMAPP). In addition, the host cell may contain a heterologous nucleic acid encoding an enzyme that may condense IPP and/or DMAPP molecules to form a polyprenyl compound. In some embodiments, the genetically modified host cell further contains a heterologous nucleic acid encoding an enzyme that may modify IPP or a polyprenyl to form an isoprenoid compound such as FPP.

Conversion of Acetyl-CoA to Acetoacetyl-CoA

The genetically modified host cell may contain a heterologous nucleic acid that encodes an enzyme that may condense two molecules of acetyl-coenzyme A to form acetoacetyl-CoA (an acetyl-CoA thiolase). Examples of nucleotide sequences encoding acetyl-CoA thiolase include (accession no. NC_000913 REGION: 2324131.2325315 (*Escherichia coli*)); (D49362 (*Paracoccus denitrificans*)); and (L20428 (*Saccharomyces cerevisiae*)).

Acetyl-CoA thiolase catalyzes the reversible condensation of two molecules of acetyl-CoA to yield acetoacetyl-CoA, but this reaction is thermodynamically unfavorable; acetoacetyl-CoA thiolysis is favored over acetoacetyl-CoA synthesis. Acetoacetyl-CoA synthase (AACS) (also referred to as acetyl-CoA:malonyl-CoA acyltransferase; EC 2.3.1.194) condenses acetyl-CoA with malonyl-CoA to form acetoacetyl-CoA. In contrast to acetyl-CoA thiolase, AACS-catalyzed acetoacetyl-CoA synthesis is essentially an energy-favored reaction, due to the associated decarboxylation of malonyl-CoA. In addition, AACS exhibits no thiolysis activity against acetoacetyl-CoA, and thus the reaction is irreversible.

In cells expressing acetyl-CoA thiolase and a heterologous ADA and/or phosphotransacetylase (PTA), the reversible reaction catalyzed by acetyl-CoA thiolase, which favors acetoacetyl-CoA thiolysis, may result in a large acetyl-CoA pool. In view of the reversible activity of ADA, this acetyl-CoA pool may in turn drive ADA towards the reverse reaction of converting acetyl-CoA to acetaldehyde, thereby diminishing the benefits provided by ADA towards acetyl-CoA production. Similarly, the activity of PTA is reversible, and thus, a large acetyl-CoA pool may drive PTA towards the reverse reaction of converting acetyl-CoA to acetyl phosphate. Therefore, in some embodiments, in order to provide a strong pull on acetyl-CoA to drive the forward reaction of ADA and PTA, the MEV pathway of the genetically modified host cell provided herein utilizes an acetoacetyl-CoA synthase to form acetoacetyl-CoA from acetyl-CoA and malonyl-CoA.

The AACS obtained from *Streptomyces* sp. Strain CL190 may be used (see Okamura et al., (2010), PNAS, vol. 107, pp. 11265-11270). Representative AACS encoding nucleic acids sequences from *Streptomyces* sp. Strain CL190 include the sequence of accession no. AB540131.1, and the corresponding AACS protein sequences include the sequence of accession nos. D7URV0 and BAJ10048. Other acetoacetyl-CoA synthases useful for the invention include those of *Streptomyces* sp. (see accession nos. AB183750; KO-3988 BAD86806; KO-3988 AB212624; and KO-2988 BAE78983); *S. anulatus* strain 9663 (see accession nos. FN178498 and CAX48662); *Actinoplanes* sp. A40644 (see accession nos. AB113568 and BAD07381); *Streptomyces* sp. C (see accession nos. NZ_ACEW010000640 and ZP_05511702); *Nocardiopsis dassonvillei* DSM 43111 (see accession nos. NZ_ABUI01000023 and ZP_04335288); *Mycobacterium ulcerans* Agy99 (see accession nos. NC_008611 and YP_907152); *Mycobacterium marinum* M (see accession nos. NC_010612 and YP_001851502); *Streptomyces* sp. Mg1 (see accession nos. NZ DS570501 and ZP_05002626); *Streptomyces* sp. AA4 (see accession nos. NZ ACEV01000037 and ZP_05478992); *S. roseosporus* NRRL 15998 (see accession nos. NZ ABYB01000295 and ZP_04696763); *Streptomyces* sp. ACTE (see accession nos. NZ_ADFD01000030 and ZP_06275834); *S. viridochromogenes* DSM 40736 (see accession nos. NZ_ACEZ01000031 and ZP_05529691); *Frankia* sp. CcI3 (see accession nos. NC_007777 and YP_480101); *Nocardia brasiliensis* (see accession nos. NC_018681 and YP_006812440.1); and *Austwickia chelonae* (see accession nos. NZ_BAGZ01000005 and ZP_10950493.1). Additional suitable acetoacetyl-CoA synthases include those described in U.S. Patent Application Publication Nos. 2010/0285549 and 2011/0281315.

Acetoacetyl-CoA synthases also useful in the compositions and methods provided herein include those molecules which are said to be "derivatives" of any of the acetoacetyl-CoA synthases described herein. Such a "derivative" has the following characteristics: (1) it shares substantial homology with any of the acetoacetyl-CoA synthases described herein; and (2) is capable of catalyzing the irreversible condensation of acetyl-CoA with malonyl-CoA to form acetoacetyl-CoA. A derivative of an acetoacetyl-CoA synthase is said to share "substantial homology" with acetoacetyl-CoA synthase if the amino acid sequences of the derivative is at least 80%, and more preferably at least 90%, and most preferably at least 95%, the same as that of acetoacetyl-CoA synthase.

Conversion of Acetoacetyl-CoA to HMG-CoA

In some embodiments, the host cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Examples of nucleotide sequences encoding such an enzyme include: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

Conversion of HMG-CoA to Mevalonate

In some embodiments, the host cell comprises a heterologous nucleotide sequence encoding an enzyme that can convert HMG-CoA into mevalonate, e.g., a HMG-CoA reductase. The HMG-CoA reductase may be an NADH-using hydroxymethylglutaryl-CoA reductase-CoA reductase. HMG-CoA reductases (EC 1.1.1.34; EC 1.1.1.88) catalyze the reductive deacylation of (S)-HMG-CoA to (R)-mevalonate, and can be categorized into two classes, class I and class II HMGrs. Class I includes the enzymes from eukaryotes and most archaea, and class II includes the HMG-CoA reductases of certain prokaryotes and archaea. In addition to the divergence in the sequences, the enzymes of the two classes also differ with regard to their cofactor specificity. Unlike the class I enzymes, which utilize NADPH exclusively, the class II HMG-CoA reductases vary in the ability to discriminate between NADPH and NADH (See, e.g., Hedl et al., (2004) *Journal of Bacteriology*, vol. 186, pp. 1927-1932). Co-factor specificities for select class II HMG-CoA reductases are provided in Table 1.

TABLE 1

| Source | Coenzyme specificity | $K_m^{NADPH}$ (μM) | $K_m^{NADH}$ (μM) |
|---|---|---|---|
| *P. mevalonii* | NADH | | 80 |
| *A. fulgidus* | NAD(P)H | 500 | 160 |
| *S. aureus* | NAD(P)H | 70 | 100 |
| *E. faecalis* | NADPH | 30 | |

HMG-CoA reductases useful for the invention include HMG-CoA reductases that are capable of utilizing NADH as a cofactor, e.g., HMG-CoA reductase from *P. mevalonii*, *A. fulgidus*, or *S. aureus*. In particular embodiments, the HMG-CoA reductase is capable of only utilizing NADH as a cofactor, e.g., HMG-CoA reductase from *P. mevalonii*, *S. pomeroyi*, or *D. acidovorans*.

In some embodiments, the NADH-using HMG-CoA reductase is from *Pseudomonas* mevalonii. The sequence of the wild-type mvaA gene of *Pseudomonas* mevalonii, which encodes HMG-CoA reductase (EC 1.1.1.88), has been previously described (see Beach and Rodwell, (1989), *J. Bacteriol.*, vol. 171, pp. 2994-3001). Representative mvaA nucleotide sequences of *Pseudomonas mevalonii* include accession number M24015. Representative HMG-CoA reductase protein sequences of *Pseudomonas mevalonii* include accession numbers AAA25837, P13702, MVAA_PSEMV.

In some embodiments, the NADH-using HMG-CoA reductase is from *Silicibacter pomeroyi*. Representative HMG-CoA reductase nucleotide sequences of *Silicibacter pomeroyi* include accession number NC_006569.1. Representative HMG-CoA reductase protein sequences of *Silicibacter pomeroyi* include accession number YP_164994.

In some embodiments, the NADH-using HMG-CoA reductase is from *Delftia acidovorans*. A representative HMG-CoA reductase nucleotide sequences of *Delftia acidovorans* includes NC_010002 REGION: complement (319980 . . . 321269). Representative HMG-CoA reductase protein sequences of *Delftia acidovorans* include accession number YP_001561318.

In some embodiments, the NADH-using HMG-CoA reductase is from *Solanum tuberosum* (see Crane et al., (2002), *J. Plant Physiol.*, vol. 159, pp. 1301-1307).

NADH-using HMG-CoA reductases useful in the practice of the invention also include those molecules which are said to be "derivatives" of any of the NADH-using HMG-CoA reductases described herein, e.g., from *P. mevalonii*, *S. pomeroyi* and *D. acidovorans*. Such a "derivative" has the following characteristics: (1) it shares substantial homology with any of the NADH-using HMG-CoA reductases described herein; and (2) is capable of catalyzing the reductive deacylation of (S)-HMG-CoA to (R)-mevalonate while preferentially using NADH as a cofactor. A derivative of an NADH-using HMG-CoA reductase is said to share "substantial homology" with NADH-using HMG-CoA reductase if the amino acid sequences of the derivative is at least 80%, and more preferably at least 90%, and most preferably at least 95%, the same as that of NADH-using HMG-CoA reductase.

As used herein, the phrase "NADH-using" means that the NADH-using HMG-CoA reductase is selective for NADH over NADPH as a cofactor, for example, by demonstrating a higher specific activity for NADH than for NADPH. The selectivity for NADH as a cofactor is expressed as a $k_{cat}^{(NADH)}/k_{cat}^{(NADPH)}$ ratio. The NADH-using HMG-CoA reductase of the invention may have a $k_{cat}^{(NADH)}/k_{cat}^{(NADPH)}$ ratio of at least 5, 10, 15, 20, 25 or greater than 25. The NADH-using HMG-CoA reductase may use NADH exclusively. For example, an NADH-using HMG-CoA reductase that uses NADH exclusively displays some activity with NADH supplied as the sole cofactor in vitro, and displays no detectable activity when NADPH is supplied as the sole cofactor. Any method for determining cofactor specificity known in the art can be utilized to identify HMG-CoA reductases having a preference for NADH as cofactor (see e.g., (Kim et al., (2000), *Protein Science, vol.* 9, pp. 1226-1234) and (Wilding et al., (2000), *J. Bacteriol., vol.* 182, pp. 5147-5152).

In some cases, the NADH-using HMG-CoA reductase is engineered to be selective for NADH over NAPDH, for example, through site-directed mutagenesis of the cofactor-binding pocket. Methods for engineering NADH-selectivity are described in Watanabe et al., (2007), *Microbiology,* vol. 153, pp. 3044-3054), and methods for determining the cofactor specificity of HMG-CoA reductases are described in Kim et al., (2000), *Protein Sci.,* vol. 9, pp. 1226-1234)A The NADH-using HMG-CoA reductase may be derived from a host species that natively comprises a mevalonate degradative pathway, for example, a host species that catabolizes mevalonate as its sole carbon source. In these cases, the NADH-using HMG-CoA reductase, which normally catalyzes the oxidative acylation of internalized (R)-mevalonate to (S)-HMG-CoA within its native host cell, is utilized to catalyze the reverse reaction, that is, the reductive deacylation of (S)-HMG-CoA to (R)-mevalonate, in a genetically modified host cell comprising a mevalonate biosynthetic pathway. Prokaryotes capable of growth on mevalonate as their sole carbon source have been described by: (Anderson et al., (1989), *J. Bacteriol,* vol. 171, pp. 6468-6472); (Beach et al., (1989), *J. Bacteriol.,* vol. 171, pp. 2994-3001); Bensch et al., *J. Biol. Chem.,* vol. 245, pp. 3755-3762); (Fimongnari et al., (1965), *Biochemistry,* vol. 4, pp. 2086-2090); Siddiqi et al., (1962), *Biochem. Biophys. Res. Commun.,* vol. 8, pp. 110-113); (Siddiqi et al., (1967), *J. Bacteriol.,* vol. 93, pp. 207-214); and (Takatsuji et al., (1983), *Biochem. Biophys. Res. Commun.,* vol. 110, pp. 187-193).

The host cell may contain both a NADH-using HMGr and an NADPH-using HMG-CoA reductase. Examples of nucleotide sequences encoding an NADPH-using HMG-CoA reductase include: (NM_206548; *Drosophila melanogaster*), (NC_002758, Locus tag SAV2545, GeneID 1122570; *Staphylococcus aureus*), (AB015627; *Streptomyces* sp. KO 3988), (AX128213, providing the sequence encoding a truncated HMG-CoA reductase; *Saccharomyces cerevisiae*), and (NC_001145: complement (115734.118898; *Saccharomyces cerevisiae*).

Conversion of Mevalonate to Mevalonate-5-Phosphate

The host cell may contain a heterologous nucleotide sequence encoding an enzyme that can convert mevalonate into mevalonate 5-phosphate, e.g., a mevalonate kinase. Illustrative examples of nucleotide sequences encoding such an enzyme include: (L77688; *Arabidopsis thaliana*) and (X55875; *Saccharomyces cerevisiae*).

Conversion of Mevalonate-5-Phosphate to Mevalonate-5-Pyrophosphate

The host cell may contain a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include: (AF429385; *Hevea brasiliensis*), (NM_006556; *Homo sapiens*), and (NC_001145. complement 712315.713670; *Saccharomyces cerevisiae*).

Conversion of Mevalonate-5-Pyrophosphate to IPP

The host cell may contain a heterologous nucleotide sequence encoding an enzyme that can convert mevalonate 5-pyrophosphate into isopentenyl diphosphate (IPP), e.g., a mevalonate pyrophosphate decarboxylase. Illustrative examples of nucleotide sequences encoding such an enzyme include: (X97557; *Saccharomyces cerevisiae*), (AF290095; *Enterococcus faecium*), and (U49260; *Homo sapiens*).

Conversion of IPP to DMAPP

The host cell may contain a heterologous nucleotide sequence encoding an enzyme that can convert IPP generated via the MEV pathway into dimethylallyl pyrophosphate (DMAPP), e.g., an IPP isomerase. Illustrative examples of nucleotide sequences encoding such an enzyme include: (NC_000913, 3031087.3031635; *Escherichia coli*), and (AF082326; *Haematococcus pluvialis*).

Polyprenyl Synthases

In some embodiments, the host cell further comprises a heterologous nucleotide sequence encoding a polyprenyl synthase that can condense IPP and/or DMAPP molecules to form polyprenyl compounds containing more than five carbons.

The host cell may contain a heterologous nucleotide sequence encoding an enzyme that can condense one molecule of IPP with one molecule of DMAPP to form one molecule of geranyl pyrophosphate ("GPP"), e.g., a GPP synthase. Non-limiting examples of nucleotide sequences encoding such an enzyme include: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha x piperita*), (AF182827; *Mentha x piperita*), (MPI249453; *Mentha x piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

The host cell may contain a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Non-limiting examples of nucleotide sequences that encode a FPP synthase include: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP 873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; Leptospira interrogans serovar *Copenhageni* str. *Fiocruz* L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP 779706; *Xylella fastidiosa* Temeculal).

In addition, the host cell may contain a heterologous nucleotide sequence encoding an enzyme that can combine IPP and DMAPP or IPP and FPP to form geranylgeranyl pyrophosphate ("GGPP"). Non-limiting examples of nucleotide sequences that encode such an enzyme include: (ATHGERPYRS; *Arabidopsis thaliana*), (BT005328; *Arabidopsis thaliana*), (NM_119845; *Arabidopsis thaliana*), (NZ AAJM01000380, Locus ZP_00743052; *Bacillus thuringiensis* serovar *israelensis*, ATCC 35646 sq1563), (CRGGPPS; *Catharanthus roseus*), (NZ AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides* f. *lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; Syntrophus aciditrophicus SB), (NC_006840, Locus YP_204095; *Vibrio fischeri* ES114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP 721015; *Streptococcus mutans* UA159).

While examples of the enzymes of the mevalonate pathway are described above, in certain embodiments, enzymes of the DXP pathway can be used as an alternative or additional pathway to produce DMAPP and IPP in the host cells, compositions and methods described herein. Enzymes and nucleic acids encoding the enzymes of the DXP pathway are well-known and characterized in the art, e.g., WO 2012/135591.

Methods of Producing Steviol Glycosides

The invention provides for the production of steviol glycosides by (a) culturing a population of any of the genetically modified host cells described herein that are capable of producing a steviol glycoside in a medium with a carbon source under conditions suitable for making the steviol glycoside compound, and (b) recovering the steviol glycoside compound from the medium.

The genetically modified host cell produces an increased amount of the steviol glycoside compared to a parent cell not having the genetic modifications, or a parent cell having only a subset of the genetic modifications, but is otherwise genetically identical. In some embodiments, the increased amount is at least 1%, 5%, 10%, 15%, 20%, 25%, 30%, 35%, 40%, 45%, 50%, 55%, 60%, 65%, 70%, 75%, 80%, 85%, 90%, 95%, 100% or greater than 100%, as measured, for example, in yield, production, and/or productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the host cell may produce an elevated level of a steviol glycoside that is greater than about 1 gram per liter of fermentation medium. In some embodiments, the host cell produces an elevated level of a steviol glycoside that is greater than about 5 grams per liter of fermentation medium. In some embodiments, the host cell produces an elevated level of a steviol glycoside that is greater than about 10 grams per liter of fermentation medium. In some embodiments, the steviol glycoside is produced in an amount from about 10 to about 50 grams, from about 10 to about 15 grams, more than about 15 grams, more than about 20 grams, more than about 25 grams, or more than about 40 grams per liter of cell culture.

In some embodiments, the host cell produces an elevated level of a steviol glycoside that is greater than about 50 milligrams per gram of dry cell weight. In some such embodiments, the steviol glycoside is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by a parent cell, on a per unit volume of cell culture basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit dry cell weight basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit volume of cell culture per unit time basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit dry cell weight per unit time basis.

In most embodiments, the production of the elevated level of steviol glycoside by the host cell is inducible by the presence of an inducing compound. Such a host cell can be manipulated with ease in the absence of the inducing compound. The inducing compound is then added to induce the production of the elevated level of steviol glycoside by the host cell. In other embodiments, production of the elevated level of steviol glycoside by the host cell is inducible by changing culture conditions, such as, for example, the growth temperature, media constituents, and the like.

Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing steviol glycosides provided herein may be performed in a suitable culture medium (e.g., with or without pantothenate supplementation) in a suitable container, including but not limited to a cell culture plate, a microtiter plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, vol. 12, pp. 398-473, Wiley-VCH Verlag GmbH & Co. KDaA, Weinheim, Germany.

In some embodiments, the culture medium is any culture medium in which a genetically modified microorganism capable of producing a steviol glycoside can subsist. The culture medium may be an aqueous medium comprising assimilable carbon, nitrogen and phosphate sources. Such a medium can also include appropriate salts, minerals, metals, and other nutrients. The carbon source and each of the essential cell nutrients may be added incrementally or continuously to the fermentation media, and each required nutrient may be maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. For example, the suitable medium may be supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

The carbon source may be a monosaccharide (simple sugar), a disaccharide, a polysaccharide, a non-fermentable carbon source, or one or more combinations thereof. Non-limiting examples of suitable monosaccharides include glucose, galactose, mannose, fructose, xylose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium may be sufficient to promote cell growth but is not so high as to repress growth of the microorganism used. Typically, cultures are run with a carbon source, such as glucose, being added at levels to achieve the desired level of growth and biomass. The concentration of a carbon source, such as glucose, in the culture medium may be greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include simple nitrogen sources, organic nitrogen sources and complex nitrogen sources. Such nitrogen sources include anhydrous ammonia, ammonium salts and substances of animal, vegetable and/or microbial origin. Suitable nitrogen sources include protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium may contain other compounds such as inorganic salts, vitamins, trace metals or growth promoters. Such other compounds may also be present in carbon, nitrogen or mineral sources in the effective medium or can be added specifically to the medium.

The culture medium may also contain a suitable phosphate source. Such phosphate sources include both inorganic and organic phosphate sources. Preferred phosphate sources include phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

The culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium may also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium may also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium may also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

The culture medium may also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media may include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, including pantothenate during the production stage of the fermentation. In some embodiments, the culture may be supplemented with relatively high concentrations of such components at the outset, for example, of the production stage, so that growth and/or steviol glycoside production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, an anti-foaming agent may be added during the culture.

The temperature of the culture medium can be any temperature suitable for growth of the genetically modified cells and/or production of steviol glycoside. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C. The pH of the culture medium can be controlled by the addition of acid or base to the culture medium. In such cases when ammonium hydroxide is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

The carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. The carbon source concentration is typically maintained below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

Other suitable fermentation medium and methods are described in, e.g., WO 2016/196321.

Fermentation Compositions

Provided herein are fermentation compositions contain a genetically modified host cell described herein and steviol glycosides produced by the genetically modified host cell. The fermentation compositions may further contain a medium. The fermentation compositions may contain a genetically modified host cell, Reb A, Reb D, and/or Reb M. The fermentation compositions provided herein may contain Reb M as a major component of the steviol glycosides produced by the genetically modified host cell. The fermentation compositions may contain Reb A, Reb D, and Reb M at a ratio of at least 1:7:50. The fermentation compositions may contain Reb A, Reb D, and Reb M at a ratio of at least 1:7:50 to 1:0.5:150. The ratio of Reb A, Reb D, and Reb M may be based on the total content of steviol glycosides that are associated with the genetically modified host cell and the medium. Alternatively, the ratio of Reb A, Reb D, and Reb M may be based on the total content of steviol glycosides in the medium. Further, the ratio of Reb A, Reb D, and Reb M may be based on the total content of steviol glycosides that are associated with the genetically modified host cell.

The fermentation compositions may contain Reb M2 at an undetectable level. In addition, the fermentation compositions may contain non-naturally occurring steviol glycosides at an undetectable level.

Recovery of Steviol Glycosides

Once the steviol glycoside is produced by the host cell, it may be recovered or isolated for subsequent use using any suitable separation and purification methods known in the art. For example, a clarified aqueous phase containing the steviol glycoside may be separated from the fermentation by centrifugation. Alternatively, a clarified aqueous phase containing the steviol glycoside may be separated from the fermentation by adding a demulsifier into the fermentation reaction. Examples of demulsifiers include flocculants and coagulants.

The steviol glycoside produced in the host cells may be present in the culture supernatant and/or associated with the host cells. Where some of the steviol glycoside is associated with the host cell, the recovery of the steviol glycoside may involve a method of improving the release of the steviol glycosides from the cells. This could take the form of washing the cells with hot water or buffer treatment, with or without a surfactant, and with or without added buffers or salts. The temperature may be any temperature deemed suitable for releasing the steviol glycosides. For example, the temperature may be in a range from 40 to 95° C.; or from 60 to 90° C.; or from 75 to 85° C. Alternatively, the temperature may be 40, 45, 50, 55, 65, 70, 75, 80, 85, 90, or 95° C. Physical or chemical cell disruption may be used to enhance the release of steviol glycosides from the host cell. Alternatively and/or subsequently, the steviol glycoside in the culture medium may be recovered using an isolation unit operations including, solvent extraction, membrane clarification, membrane concentration, adsorption, chromatography, evaporation, chemical derivatization, crystallization, and drying.

Methods of Making Genetically Modified Cells

Also provided herein are methods for producing a host cell that is genetically engineered to contain one or more of the modifications described above, e.g., one or more heterologous nucleic acids encoding kaurenoic acid hydroxylase, and/or biosynthetic pathway enzymes, e.g., for a steviol glycoside compound. Expression of a heterologous enzyme in a host cell can be accomplished by introducing into the host cells a nucleic acid comprising a nucleotide sequence encoding the enzyme under the control of regulatory elements that permit expression in the host cell. The nucleic acid may be an extrachromosomal plasmid, a chromosomal integration vector that can integrate the nucleotide sequence into the chromosome of the host cell, or a linear piece of double stranded DNA that can integrate via homology the nucleotide sequence into the chromosome of the host cell.

Nucleic acids encoding these proteins can be introduced into the host cell by any method known to one of skill in the art (see, e.g., Hinnen et al., (1978) *Proc. Natl. Acad. Sci. USA*, vol. 75, pp. 1292-1293; Cregg et al., (1985), *Mol. Cell. Biol.*, vol. 5, pp. 3376-3385; Goeddel et al. eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include, spheroplasting, electroporation, PEG 1000 mediated transformation, and lithium acetate or lithium chloride mediated transformation.

The amount of an enzyme in a host cell may be altered by modifying the transcription of the gene that encodes the enzyme. This can be achieved by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively, or in addition, the copy number of an enzyme in a host cell may be altered by modifying the level of translation of an mRNA that encodes the enzyme. This can be achieved by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell may be altered in a number of ways, including expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower $K_{cat}$ or a lower or higher $K_m$ for the substrate, expressing a modified form of the enzyme that has a higher or lower thermostability, expressing a modified form of the enzyme that has a higher or lower activity at the pH of the cell, expressing a modified form of the enzyme that has a higher or lower accumulation in a subcellular compartment or organelle, expressing a modified form of the enzyme that has increased or decreased ability to insert into or associate with cellular membranes, expressing a modified form of the enzyme that has a higher or lower affinity for accessory proteins needed to carry out a reaction, expressing a modified form of the enzyme that has a higher or lower affinity for necessary cofactors or ligands, expressing a modified form of the enzyme that has a increased or decreased space in the active site (thereby differentially allowing or excluding different substrates for the reaction), or expressing an altered form of the enzyme that is more or less affected by feed-back or feed-forward regulation by another molecule in the pathway.

A nucleic acid used to genetically modify a host cell may contain one or more selectable markers useful for the selection of transformed host cells and for placing selective pressure on the host cell to maintain the foreign DNA.

The selectable marker may be an antibiotic resistance marker. Examples of antibiotic resistance markers include the BLA, NAT1, PAT, AUR1-C, PDR4, SMR1, CAT, mouse dhfr, HPH, DSDA, $KAN^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the $KAN^R$ gene of the Tn903 transposon confers resistance to G418; and the SH BLE gene product from Streptoalloteichus hindustanus confers resistance to Zeocin (bleomycin). The antibiotic resistance marker may be deleted after the genetically modified host cell disclosed herein is isolated.

The selectable marker may function by rescue of an auxotrophy (e.g., a nutritional auxotrophy) in the genetically modified microorganism. In auxotrophy, a parent microorganism contains a functional disruption in one or more gene products that function in an amino acid or nucleotide biosynthetic pathway and that renders the parent cell incapable of growing in media without supplementation with one or more nutrients. Such gene products include the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. The selectable marker may rescue other non-lethal deficiencies or phenotypes that can be identified by a known selection method.

Described herein are specific genes and proteins useful in the methods, compositions, and host cells of the invention; however, the absolute identity to such genes is not necessary. For example, changes in a particular gene or polynucleotide containing a sequence encoding a polypeptide or enzyme can be performed and screened for activity. Typically, such changes involve conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides may also be used to express the enzymes.

It can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias." Codon optimization for other host cells can be readily determined using codon usage tables or can be performed using commercially available software, such as CodonOp from Integrated DNA Technologies.

Optimized coding sequences containing codons preferred by a particular prokaryotic or eukaryotic host (Murray et al., (1989), *Nucl Acids Res.*, vol. 17, pp. 477-508) can be prepared, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., (1996), *Nucl Acids Res., vol.* 24, pp. 216-218).

Due to the degenerate nature of the genetic code, a variety of DNA molecules differing in their nucleotide sequences may be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the invention. In similar fashion, a polypeptide can typically tolerate one or more amino acid substitutions, deletions, and insertions in its amino acid sequence without loss or significant loss of a desired activity. The invention includes such polypeptides with different amino acid sequences than the specific proteins described herein so long as the modified or variant polypeptides have the enzymatic activity of the reference polypeptide. Furthermore, the amino acid sequences encoded by the DNA sequences shown herein merely illustrate examples of the invention.

In addition, homologs of enzymes useful for the practice of the compositions, methods, or host cells are encompassed by the invention. Two proteins (or a region of the proteins) are considered to be substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes may be at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., (1994), *Methods in Mol Biol*, vol. 25, pp. 365-389).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used for comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes or any of the regulatory elements that control or modulate their expression may be optimized by genetic/protein engineering techniques, such as directed evolution or rational mutagenesis. Such action allows those of ordinary skill in the art to optimize the enzymes for expression and activity in yeast.

In addition, genes encoding these enzymes can be identified from other fungal and bacterial species and can be expressed for the modulation of the steviol glycoside pathway. A variety of organisms may serve as sources for these enzymes, including *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorpha*, *Candida* spp., *Trichosporon* spp., *Yamadazyma* spp., including *Y.* spp. *stipitis*, *Torulaspora pretoriensis*, *Issatchenkia orientalis*, *Schizosaccharomyces* spp., including *S. pombe*, *Cryptococcus* spp., *Aspergillus* spp., *Neurospora* spp., or *Ustilago* spp. Sources of genes from anaerobic fungi include *Piromyces* spp., *Orpinomyces* spp., or *Neocallimastix* spp. Sources of prokaryotic enzymes that are useful include *Escherichia. coli*, *Zymomonas mobilis*, *Staphylococcus aureus*, *Bacillus* spp., *Clostridium* spp., *Corynebacterium* spp., *Pseudomonas* spp., *Lactococcus* spp., *Enterobacter* spp., and *Salmonella* spp.

Techniques known to those skilled in the art may be suitable to identify additional homologous genes and enzymes. Generally, analogous genes and/or analogous enzymes can be identified by functional analysis and will have functional similarities. Techniques known to be suitable to identify analogous genes and analogous enzymes include PCR, degenerate PCR, low stringency nucleic acid hybridization, expression cloning, and high through-put screening. For example, to identify homologous or analogous UDP glycosyltransferases, KAH, or any steviol glycoside biosynthetic pathway genes, proteins, or enzymes, techniques may include, but are not limited to, cloning a gene by PCR using primers based on a published sequence of a gene/enzyme of interest, or by degenerate PCR using degenerate primers designed to amplify a conserved region among a gene of interest. Further, one may use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., *Branched-Chain Amino Acids Methods Enzymology*, 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above-mentioned databases in accordance with the teachings herein.

EXAMPLES

Example 1: Yeast Transformation Methods

Each DNA construct was integrated into *Saccharomyces cerevisiae* (CEN.PK113-7D) using standard molecular biology techniques in an optimized lithium acetate (LiAc) transformation. Briefly, cells were grown overnight in yeast extract peptone dextrose (YPD) media at 30° C. with shaking (200 rpm), diluted to an $OD_{600}$ of 0.1 in 100 mL YPD, and grown to an $OD_{600}$ of 0.6-0.8. For each transformation, 5 mL of culture was harvested by centrifugation, washed in 5 mL of sterile water, spun down again, resuspended in 1 mL of 100 mM LiAc, and transferred to a microcentrifuge tube. Cells were spun down (13,000 xg) for 30 seconds, the supernatant was removed, and the cells were resuspended in a transformation mix consisting of 240 μL 50% PEG, 36 μL 1 M LiAc, 10 μL boiled salmon sperm DNA, and 74 μL of donor DNA. For transformations that required expression of the endonuclease F-Cph1, the donor DNA included a plasmid carrying the F-CphI gene expressed under the yeast TDH3 promoter for expression. The expression of the F-CphI endonuclease results in the cleavage of the endonuclease recognition site in the landing pad thereby facilitating integration of the target gene of interest. Following a heat shock at 42° C. for 40 minutes, cells were recovered overnight in YPD media before plating on selective media. DNA integration was confirmed by colony PCR with primers specific to the integrations.

Example 2: Generation of a Base Strain Capable of High Flux to Farnesylpyrophosphate (FPP) and the Isoprenoid Farnesene A farnesene production strain was generated from a wild-type *Saccharomyces cerevisiae* strain (CEN.PK113-7D) by expressing the genes encoding the mevalonate pathway enzymes under control of native GAL1 or GAL10 promoters. This strain comprised the following chromosomally integrated mevalonate pathway genes from *S. cerevisiae*: acetyl-CoA thiolase, HMG-CoA synthase, HMG-CoA reductase, mevalonate kinase, phosphomevalonate kinase, mevalonate pyrophosphate decarboxylase, and IPP:DMAPP isomerase. In addition, the strain contains multiple copies of farnesene synthase from *Artemisinin annua* under control of either native GAL1 or GAL10 promoters. All heterologous genes were codon optimized using publicly available or other suitable algorithms. The strain also contained a deletion of the GAL80 gene. Examples of methods of creating *S. cerevisiae* strains with high flux to isoprenoids are described in the U.S. Pat. Nos. 8,415,136 and 8,236,512 which are incorporated herein in their entireties.

Figure 2:
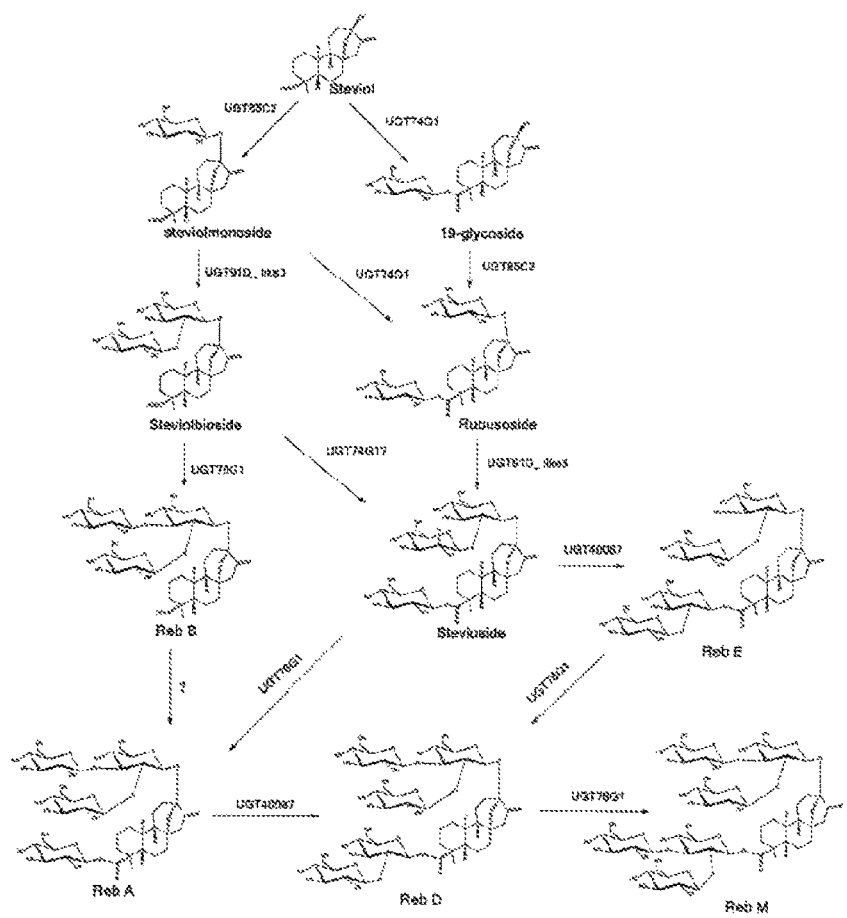
FIG. 2 is a diagram of the biochemical pathways for steviol glycoside, including RebM, production from steviol.

Example 3: Creation of a Strain for the Rapid Screening of UGT76G1 with Higher Activity to Convert Rebaudioside D to Rebaudioside M FIG. 1 shows an exemplary biosynthetic pathway from FPP to steviol. FIG. 2 shows an exemplary biosynthetic pathway from steviol to the glycoside RebM. The farnesene base strain described above was further engineered to have high flux to the C-20 isoprenoid kaurene by integrating four copies of geranylgeranylpyrophosphate synthase (GGPPS) encoding genes into the genome, followed by two copies of a copalyldiphosphate synthase encoding genes, and one copy of a kaurene synthase encoding gene. Subsequently, all copies of farnesene synthase were removed from the strain and the strain was confirmed to produce ent-kaurene and no farnesene. This ent-kaurene strain was then transformed with all the remaining genes necessary to convert ent-kaurene to Rebaudioside M to make Strain 1 (Table 1). Each gene after the ent-kaurene synthase was integrated as a single copy, except for Sr.KAH encoding gene has six copies integrated.

In addition to the genes necessary to produce Rebaudioside M (RebM) from FPP, one copy of heterologous DNA encoding BPT1 (SEQ ID NO: 15) under control of the GAL1 promoter was integrated into the genome of Strain 1. BPT1 is a native yeast vacuolar ABC transporter that, when overexpressed, increases RebM titers and total steviol glycoside titers. However, while overexpression of BPT1 results in higher RebM titers overall, it also doubled the amount of Rebaudioside D (RebD) produced, causing a significant reduction in the ratio of RebM:RebD. Of all the steviol glycosides comprising the RebM pathway (FIG. 2), RebD is the most difficult to purify away from RebM, given RebD's similarity in weight and structure to RebM (the two compounds only differ by one glucose molecule). To generate the highest purity, best tasting, and lowest cost RebM, it is critical to have very high UGT76G1 mediated catalysis of RebD to RebM, i.e. maximal RebM and minimal RebD.

BPT1 has a higher affinity for RebD than wild type UGT76G1 thereby out-competing wild type UGT76G1 for substrate. We sought to find enhanced alleles of UGT76G1 that would have higher affinity for the RebD substrate than BPT1 and thereby convert more RebD to RebM.

TABLE 1

Genes, Promoters, and Amino Acid sequences of the Enzymes used to Convert FPP to RebM.

| Enzyme | SEQ ID NOs | Promoter |
| --- | --- | --- |
| Bt.GGPPS | SEQ ID NO: 3 | PGAL1 |
| Ent-Os.CDPS | SEQ ID NO: 4 | PGAL1 |
| Ent-Pg.KS | SEQ ID NO: 5 | PGAL1 |

TABLE 1-continued

Genes, Promoters, and Amino Acid sequences of the Enzymes used to Convert FPP to RebM.

| Enzyme | SEQ ID NOs | Promoter |
|---|---|---|
| PS.KO | SEQ ID NO: 6 | PGAL1 |
| At.CPR | SEQ ID NO: 7 | PGAL3 |
| Sr.KAH | SEQ ID NO: 8 | PGAL1 |
| UGT85C2 | SEQ ID NO: 9 | PGAL10 |
| UGT74G1 | SEQ ID NO: 10 | PGAL1 |
| UGT91D_like3 | SEQ ID NO: 11 | PGAL1 |
| UGT76G1 | SEQ ID NO: 1 | PGAL1 |
| UGT40087 | SEQ ID NO: 12 | PGAL1 |

Strain 1 overexpressing BPT1 was further transformed with a landing pad (FIG. 3) to allow for the rapid insertion of mutated UGT76G1 alleles in order to screen for higher RebD to RebM conversion activity; this was termed Strain 2. The landing pad consists of 500 bp of locus-targeting DNA sequences on either end of the construct to the genomic region upstream and downstream of the yeast ALD5 gene, thereby deleting the ALD5 gene when the landing pad is integrated into the yeast chromosome. Internally, the landing pad contains a PGAL1 promoter and a yeast terminator (tHEM13) flanking an endonuclease recognition site (F-CphI).

Example 4: Yeast Culturing Conditions

Yeast colonies transformed with mutated UGT76G1 alleles were picked into 96-well microtiter plates containing Bird Seed Media (BSM, originally described by van Hoek et al., (2000), *Biotechnology and Bioengineering*, vol. 68, pp. 517-523) with 20 g/L sucrose, 3.75 g/L ammonium sulfate, and 5 g/L lysine. Cells were cultured at 30° C. in a high capacity microtiter plate incubator shaking at 1000 rpm and 80% humidity for 3 days until the cultures reached carbon exhaustion. The growth-saturated cultures were subcultured into fresh plates containing modified BSM media (25% concentration of all components except the buffer and carbon source), with 40 g/L sucrose, 3.75 g/L ammonium sulfate, and 1 g/L lysine by taking 14.4 µl from the saturated cultures and diluting into 360 µl of fresh media. Cells in the production media were cultured at 30° C. in a high capacity microtiter plate shaker at 1000 rpm and 80% humidity for an additional 3 days prior to extraction and analysis.

Example 5: Whole Cell Broth Sample Preparation Conditions for Analysis of Steviol Glycosides To analyze the amount of each of the steviol glycosides produced in the culture, upon culturing completion the whole cell broth was diluted with 628 µL of 100% ethanol, sealed with a foil seal, and shaken at 1250 rpm for 30 seconds to extract the steviol glycosides. 314 µL of water was added to each well directly to dilute the extraction. The plate was briefly centrifuged to pellet solids. 208 µl of 50:50 ethanol:water containing 0.48 mg/L rebaudioside N was transferred to a new 250 µl assay plate and 2 µL of the culture/ethanol mixture was added to the assay plate. A foil seal was applied to the plate prior to analysis.

Example 6: Analytical Methods

Samples for steviol glycoside measurements were analyzed by mass spectrometer (Agilent 6470-QQQ) with a RapidFire 365 system autosampler with C8 cartridge using the configurations shown in Tables 2 and 3.

TABLE 2

RapidFire 365 System Configuration

| | |
|---|---|
| Pump 1, Line A: 2 mM Ammonium formate in water | 100% A, 1.5 mL/min |
| Pump 2, Line A: 35% acetonitrile in water | 100% A, 1.5 mL/min |
| Pump 3, Line A: 80% acetonitrile in water | 100% A, 0.8 mL/min |
| State 1: Aspirate | 600 ms |
| State 2: Load/Wash | 3000 ms |
| State 3: Extra was | 1500 ms |
| State 4: Elute | 5000 ms |
| State 5: Reequilibrate | 1000 ms |

TABLE 3

6470-QQQ MS Method Configuration

| | |
|---|---|
| Ion Source | AJS ESI |
| Time Filtering peak width | 0.02 min |
| Stop Time | No limit/as pump |
| Scan Type | MRM |
| Diverter Valve | To MS |
| Delta EMV | (+)0/(−)300 |
| Ion Mode (polarity) | Negative |
| Gas Temp | 250° C. |
| Gas Flow | 11 L/min |
| Nebulizer | 30 psi |
| Sheath Gas Temp | 350° C. |
| Sheath Gas Flow | 11 L/min |
| Negative Capillary V | 2500 V |

The peak areas from a chromatogram from a mass spectrometer were used to generate the calibration curve. The molar ratios of relevant compounds were determined by quantifying the amount in moles of each compound through external calibration using an authentic standard, and then taking the appropriate ratios.

Example 7: Evolving UGT76G1 to have Higher Activity to Convert Rebaudioside D to Rebaudioside A UGT76G1 is capable of transferring a glucose moiety to the C-3' position of a steviol glycoside (where glycoside=Glcb(1→2)Glc). This chemistry can occur at either the C-13-O-linked glucose of the acceptor molecule, or the C-19-O-linked glucose of the acceptor molecule. Accordingly, UGT76G1 is capable of functioning as a uridine 5'-diphospho glucosyltransferase to the: (1)C-3' position of the 13-O-linked glucose on steviolbioside in a β(1→2) linkage forming Reb B, (2)C-3' position of the 19-O-linked glucose on stevioside in a β(1→2) linkage forming Reb A, and (3)C-3' position of the 19-O-linked glucose on RebD in a β(1→2) linkage forming RebM. UGT76G1 has been described in Richman et al., 2005, *Plant J.*, vol. 41, pp. 56-67; US2014/0329281; WO2016/038095; and accession no. AAR06912.1.

In the synthesis of RebM, UGT76G1 acts on a number of different steviol glycosides to add a glucose moiety to the C-3' position of a acceptor molecule a steviol glycoside (where glycoside=Glcb(1→2)Glc). For example, UGT76G1 can act on steviolbioside (to form rebaudioside B), stevioside (to form rebaudioside A), rebaudioside E (to form rebaudioside D), and rebaudioside D (to from rebaudioside M). All these native enzyme functions can be used to produce RebM, but the two most critical enzyme functions of UGT76G1 are glycosylating stevioside to form rebaudioside A and glycosylating rebaudioside D to from rebaudioside M (FIG. 2).

Figure 4:
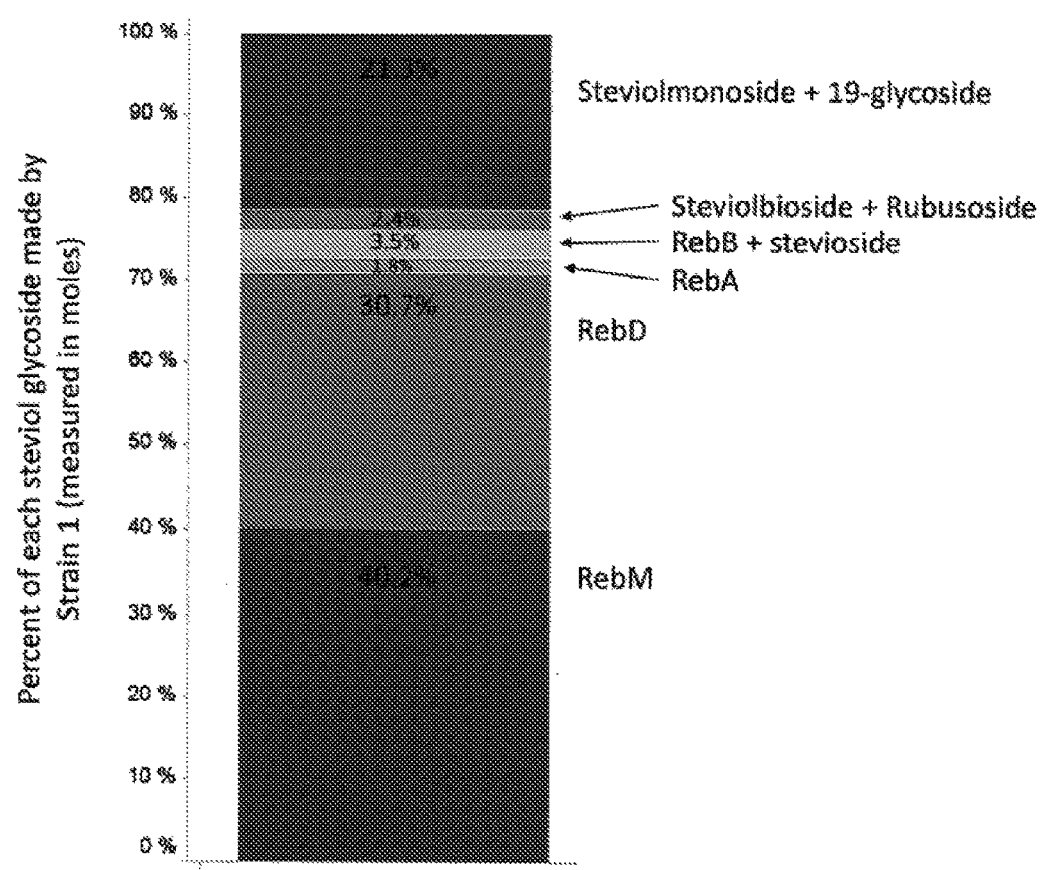
FIG. 4 is a graph showing the percent of each steviol glycoside made by strain 1.

Strain 2 described in example 3 contains a single copy of wild type UGT76G1 sequence and overexpressed BPT1. This strain makes primarily the high molecular weight glycosides RebD and RebM. On a molar basis, RebD and RebM make up approximately 70% of the total steviol glycosides, with stevioside only making up at most 3.5% of the total steviol glycosides (FIG. 4). The ratio of RebM:RebD is 1.3:1 or nearly 50/50 (FIG. 4). This indicates that wild type UGT76G1 is very efficient at converting stevioside to RebA, but it much less efficient at converting RebD to RebM in the presence of overexpressed BPT1. This makes intuitive sense, since the plant *Stevia rebaudiana* makes mostly RebA due to the fact that the native enzyme in *Stevia rebaudiana* that converts RebA to RebD (UGT91D) has very low activity on RebA. Therefore very little RebD is made in planta, and RebD is not the primary substrate for native UGT76G1.

Strain 2 was built to screen for mutated versions of UGT76G1 that increase RebD to RebM conversion, but not affect the high conversion rate of stevioside to RebA. To do this, there is still a single wt version of UGT76G1 in strain 2 to perform all upstream reactions, while containing a landing pad (FIG. 3) to rapidly insert and screen novel UGT76G1 mutant alleles for better RebD to RebM activity. This strategy is fundamentally different from previous strategies to evolve UGT76G1 in that we are attempting to diverge UGT76G1 function and generate separate alleles for different biosynthetic transformations. We are also specifically evolving the UGT76G1 protein in the context of the overexpressed BPT1 ABC transporter, so we are screening for improvements in UGT76G1 that will be able to outcompete BPT1 for the substrate RebD. This type of in vivo screen is significantly superior to a traditional in vitro screen for just improving a single enzymatic function (here RebD to RebM conversion) because the in vivo screen will find and eliminate any mutated UGT76G1 alleles that interfere with stevioside to RebA conversion in the host cell (or any other interfering reaction upstream of RebD to RebM).

To do this screen, a yeast-codon optimized DNA sequence (SEQ ID NO: 2) for wt UGT76G1 protein was generated and the corresponding synthetic DNA sequence was used as the template for a site saturation mutagenesis library. Each amino acid residue in UGT76G1 was mutated using various degenerate codons. Degenerate codons consisted of NDT combined with VHG; where N stands for any nucleotide Adenine, Thymine, Guanine, and Cytosine; D stands for Adenine, Guanine, and Thymine; T stands for Thymine; V represents Adenine, Cytosine, or Guanine; H represents Adenine, Cytosine, or Thymine; and G represents Guanine. The degenerate codon NDT is able to encode 12 different amino acids (R,N,D,C,G, H,I, L,F,S,Y, and V) in equal amounts whereas the degenerate codon VHG is able to encode 9 different amino acids (A, E, K, L, M, P, Q, T, and V). When VHG and NDT are mixed in a ratio of 3:4, all amino acids with the exception of tryptophan are represented in a roughly equimolar amount. The library was constructed via PCR. Each PCR product contains a mixture of codons targeted to mutate a single protein residue, as well as 40 bp of flanking homologous sequences at both promoter and terminator regions of the landing pad in Strain 2. Each variant pool, representing changes at a single amino acid in UGT76G1 was transformed independently into Strain 2, and the total steviol glycosides produced were measured as described above.

For screening genes for improved RebD to RebM activity, all of the steviol glycosides in the whole cell broth produced by a strain were extracted and measured via mass spectrometry. For Tier 1 screening, 28 colonies were chosen per site to screen, roughly representing a 1.5× sampling rate of the library. 96 amino acids in the wild type UGT76G1 was subjected to mutagenesis and screening as described. Control strains had an extra copy of wild type UGT76G1 inserted in the landing pad. Hits were promoted to a Tier 2 screen if the Tier 1 screen showed an increase in the amount of RebM produced over parent.

Upon finding mutations in UGT76G1 that appeared to increase activity of the enzyme for RebD to RebM conversion in vivo, a Tier 2 screen was performed with higher replication (N≥5) to confirm the improvement by plating each hit and picking two separate isolates that were each measured for steviol glycoside production with multiple replicates. A mutation was confirmed to improve UGT76G1 activity if the amount of RebM produced by the mutant was at least one standard deviation above the median amount of RebM produced by the control strain (with a second copy of wild type UGT76G1 protein).

Figure 5:
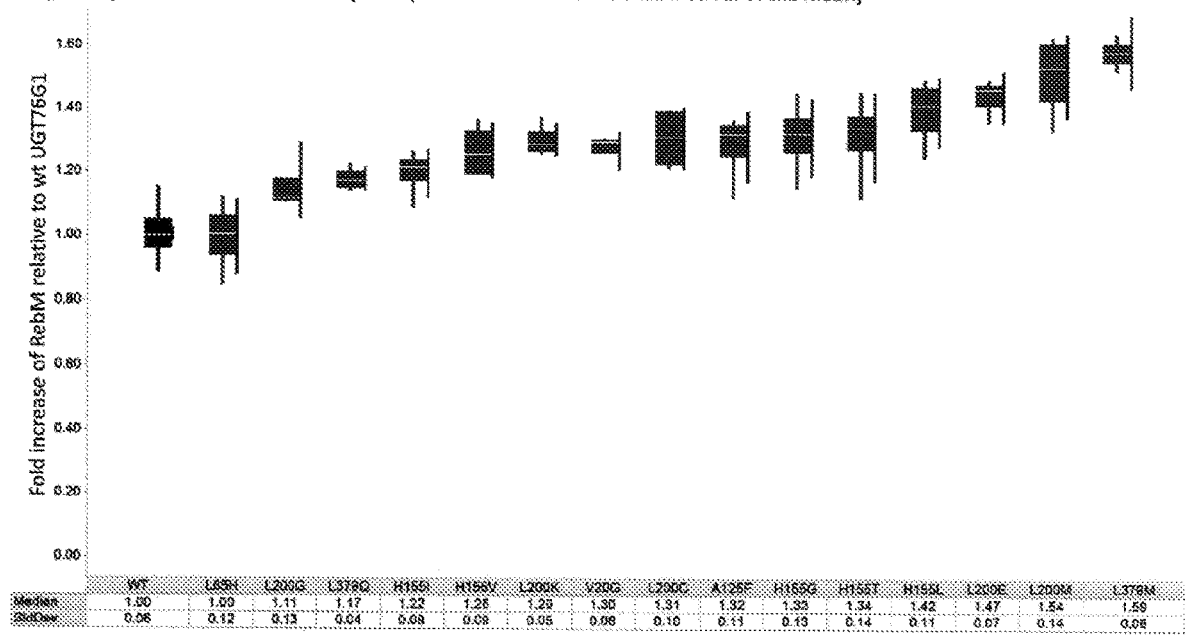
FIG. 5 is a graph showing the fold increase in Reb M production for strains expressing variant UGT76G1 enzymes relative to wild-type UGT76G1. Dark lines next to box plots represent 95% confidence intervals of the mean.
Figure 6:
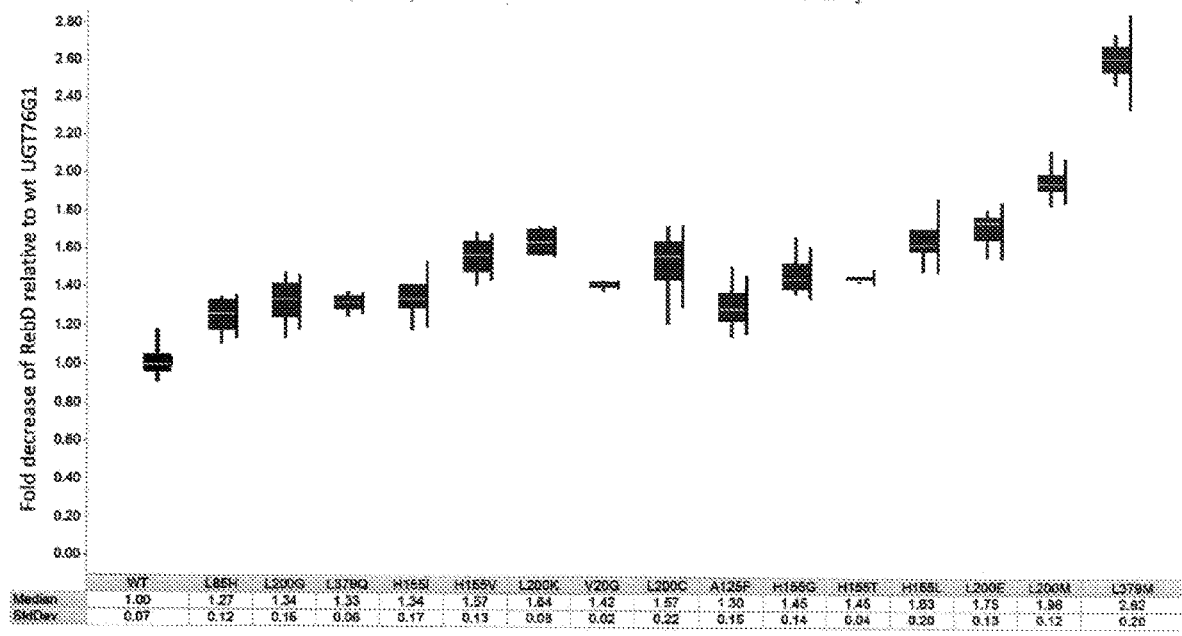
FIG. 6 is a graph showing the fold decrease in Reb D production for strains expressing variant UGT76G1 enzymes relative to wild-type UGT76G1. Dark lines next to box plots represent 95% confidence intervals of the mean.
Figure 7:
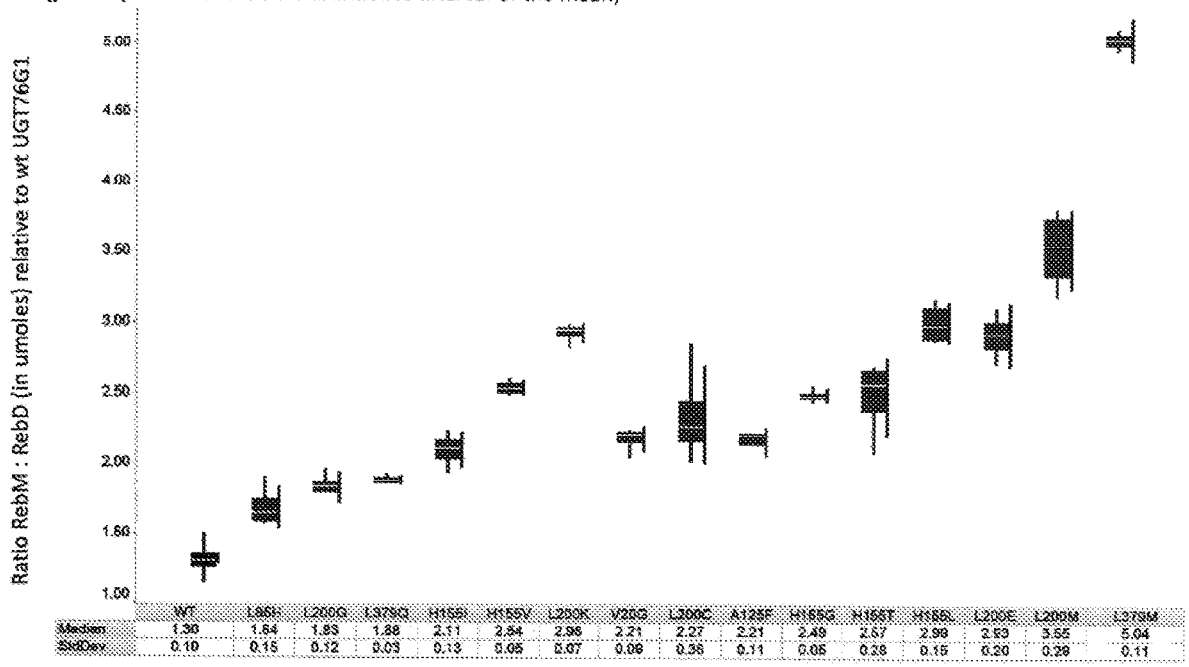
FIG. 7 is a graph showing the ratio of (Reb M/Reb D) produced by strains expressing variant UGT76G1 enzymes relative to wild-type UGT76G1. Dark lines next to box plots represent 95% confidence intervals of the mean.
Figure 8:
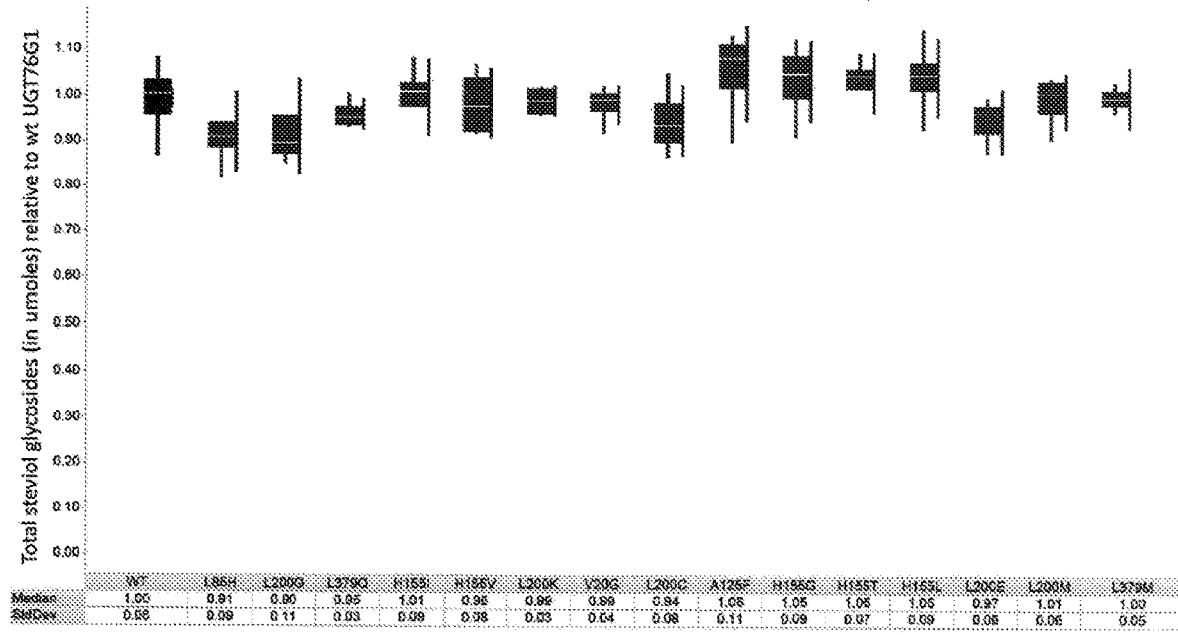
FIG. 8 is a graph showing total steviol glycosides produced by strains expressing variant UGT76G1 enzymes relative to wild-type UGT76G1. Dark lines next to box plots represent 95% confidence intervals of the mean.
Figure 9:
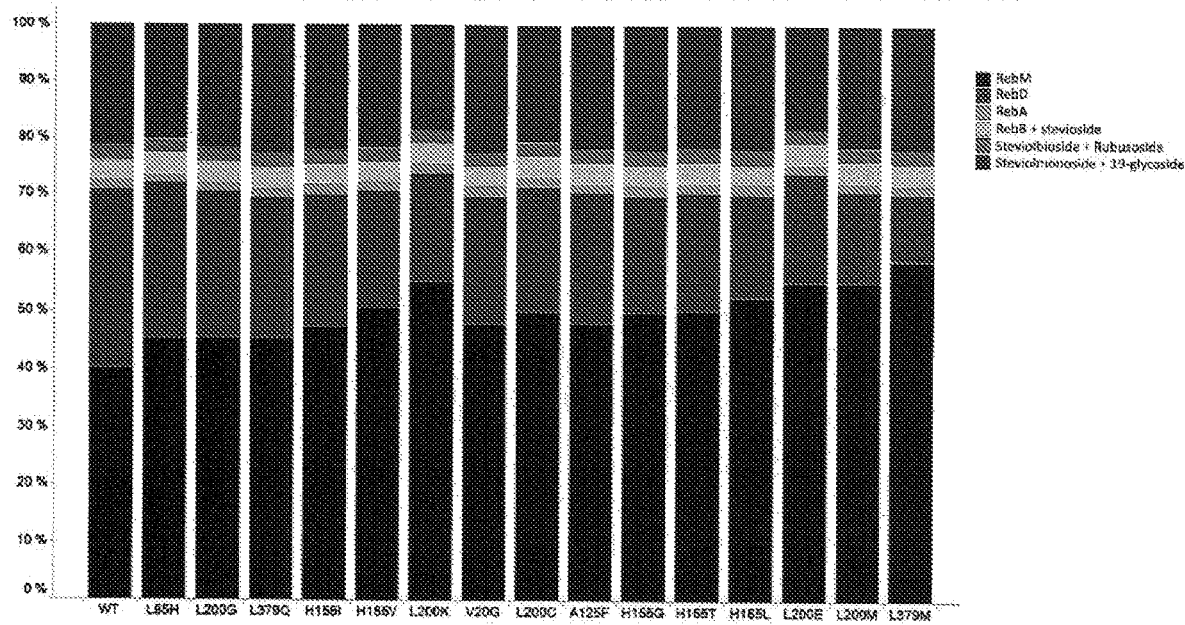
FIG. 9 is a graph showing the relative amounts of various steviol glycosides made in each of several strains expressing variant UGT76G1 enzymes relative to wild-type UGT76G1.

In total, 15 unique mutations were found that increased RebM titers and/or decreased RebD titers that lead to a significant increase in the ratio of RebM/RebD (as measured in umoles) (FIGS. 5, 6, 7, and Table 4). Total steviol glycosides (TSG) is calculated by summing all the steviol glycosides produced in the strain (in μmoles); the improved mutant alleles of UGT76G1 did not significantly change the TSG produced by the strain (FIG. 8). Finally, while the ratio of RebM/RebD increased, the amount of stevioside did not significantly change in the strains with a mutated second copy of UGT76G1 (FIG. 9). This data confirms that the new UGT76G1 mutant alleles do not interfere with the wild type copy of UGT76G1, they do not interfere with conversion of stevioside to RebA, and they outcompete overexpressed BPT1 for the substrate RebD.

TABLE 4

List of all UGT76G1 Mutations that increase RebM titers and/or decrease RebD titers without affecting the total steviol glycosides produced.

| Mutation | Mutant | TSG | Fold increase in Reb M | Fold decrease in Reb D |
| --- | --- | --- | --- | --- |
| wild type control | NA | 1 | 1 | 1 |
| L85H | 1 | 0.91 | 1 | 1.27 |
| L200G | 2 | 0.9 | 1.11 | 1.34 |
| L379Q | 3 | 0.95 | 1.17 | 1.33 |
| H155I | 4 | 1.01 | 1.22 | 1.34 |
| H155V | 5 | 0.98 | 1.26 | 1.57 |
| L200K | 6 | 0.99 | 1.29 | 1.64 |
| V20G | 7 | 0.99 | 1.3 | 1.42 |
| L200C | 8 | 0.94 | 1.31 | 1.57 |
| A125F | 9 | 1.08 | 1.32 | 1.3 |
| H155G | 10 | 1.05 | 1.33 | 1.45 |
| H155T | 11 | 1.05 | 1.34 | 1.45 |
| H155L | 12 | 1.05 | 1.42 | 1.63 |
| L200E | 13 | 0.97 | 1.47 | 1.75 |
| L200M | 14 | 1.01 | 1.54 | 1.96 |
| L379M | 15 | 1 | 1.59 | 2.62 |

Figure 3:
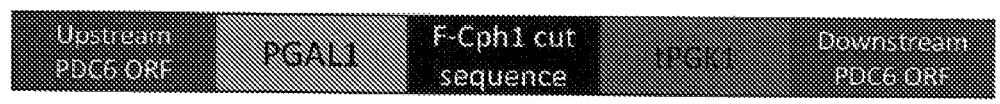
FIG. 3 is a diagram of the landing pad structure with the F-Cph1 recognition site.

Example 8: Combination of Single UGT76G1 Mutants Lead to Increased RebD to RebM Conversion Activity Single UGT76G1 mutants improved for Reb D to RebM conversion as identified from the SSM library of 96 residues described in example 7 and table 4 were combined in a full factorial fashion to yield a library with a theoretical size of 864 combinations. Sets of PCR primers were ordered that would amplify different parts of the UGT76G1 protein such that each part contained one of the mutations at the 6 different positions listed in table 4. The individual PCR products were then combined so that an equal representation of parts were included; overlap extension PCR was used to assemble all the pieces into a library of full length UGT76G1 alleles. The resulting pool of alleles had overlapping homologous DNA to the promoter and terminator of the landing pad (FIG. 3). The pool of UGT76G1 variants were then transformed into Strain 2 and inserted into the landing pad via homologous recombination. This combinatorial UGT76G1 mutant library was screened at 2.5× coverage. The same Tier 1 and Tier 2 screening approach was applied as described for the single site saturation mutagenesis screen in example 7. The only difference was that N≥6 replicates were screened in Tier 2 for the combinatorial mutant library.

Figure 10:
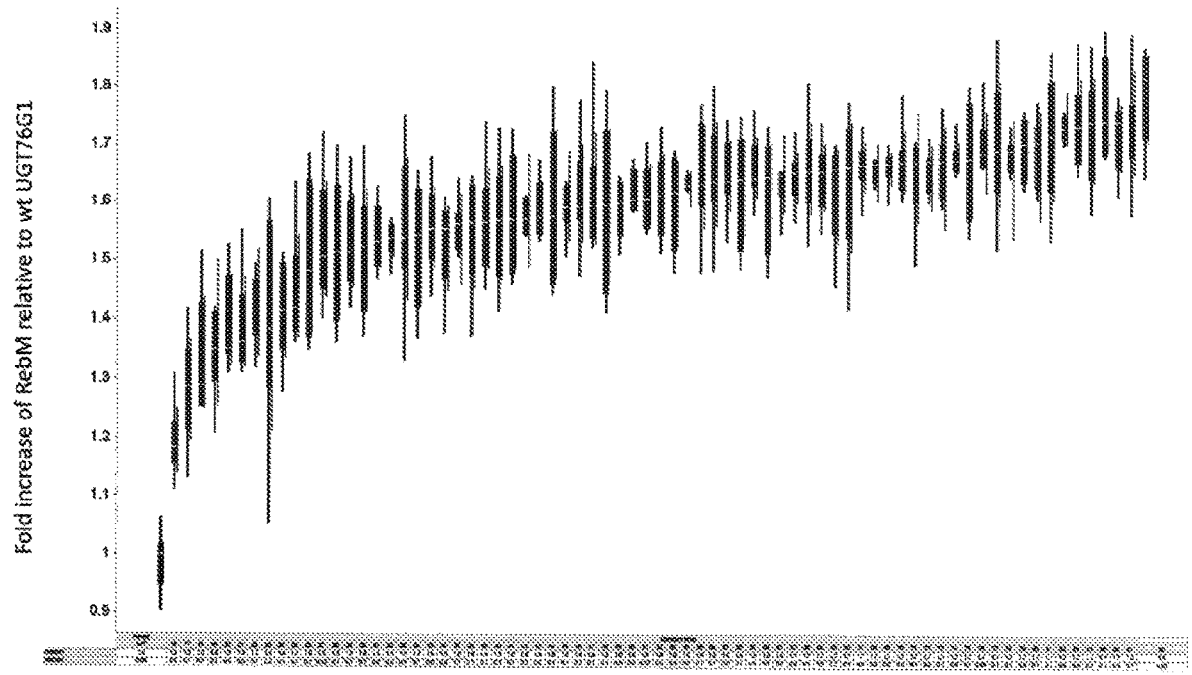
FIG. 10 is a graph showing the fold increase in Reb M production for strains expressing variant UGT76G1 enzymes relative to wild-type UGT76G1. Dark lines next to box plots represent 95% confidence intervals of the mean.
Figure 11:
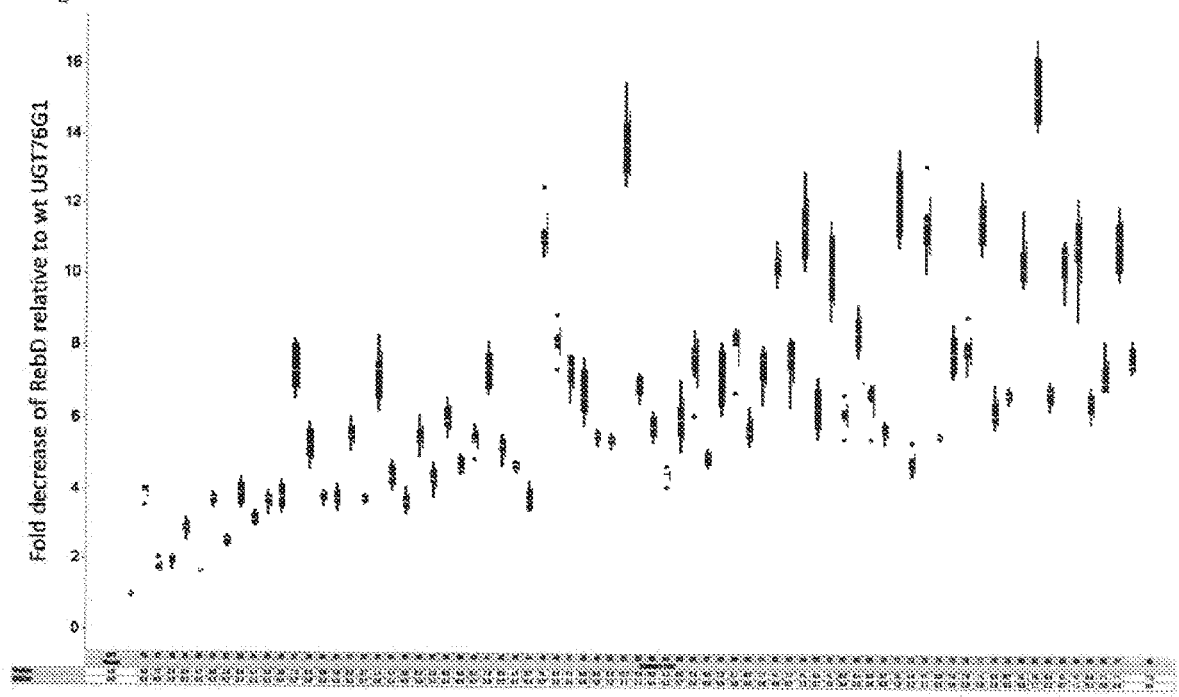
FIG. 11 is a graph showing the fold decrease in Reb D production for strains expressing variant UGT76G1 enzymes relative to wild-type UGT76G1. Dark lines next to box plots represent 95% confidence intervals of the mean.
Figure 12:
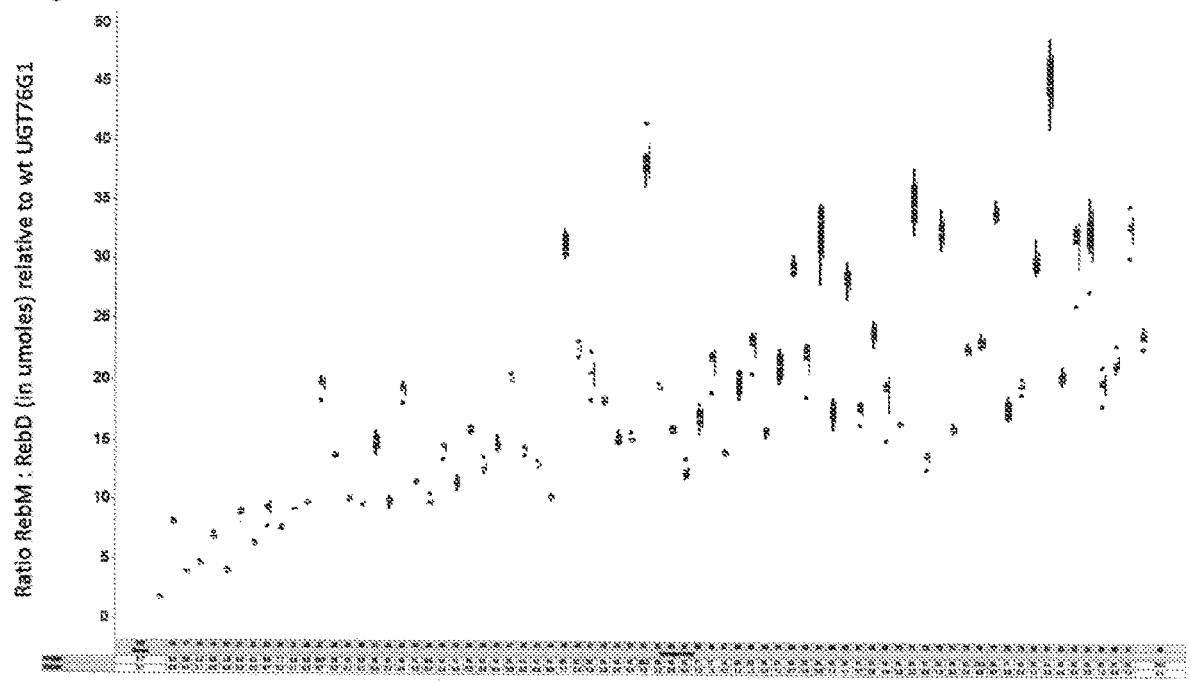
FIG. 12 is a graph showing the ratio of (Reb M/Reb D) produce by strains expressing variant UGT76G1 enzymes relative to wild-type UGT76G1. Dark lines next to box plots represent 95% confidence intervals of the mean.
Figure 13:
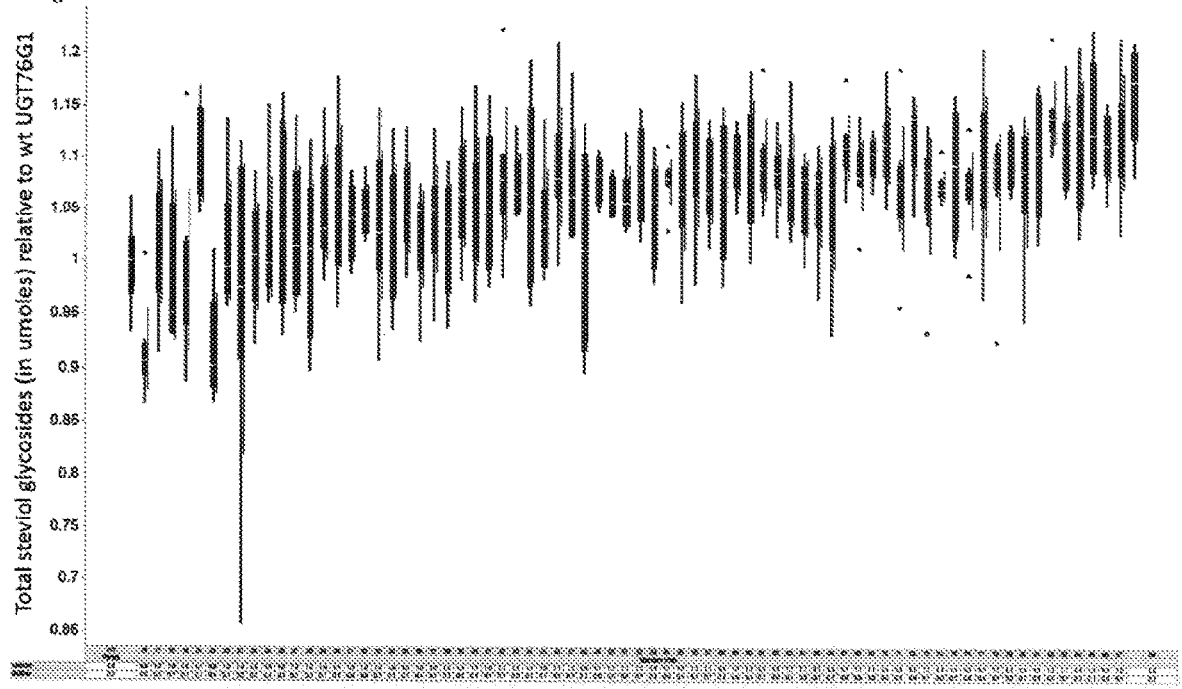
FIG. 13 is a graph showing total steviol glycosides produced by strains expressing variant UGT76G1 enzymes relative to wild-type UGT76G1. Dark lines next to box plots represent 95% confidence intervals of the mean.
Figure 14:
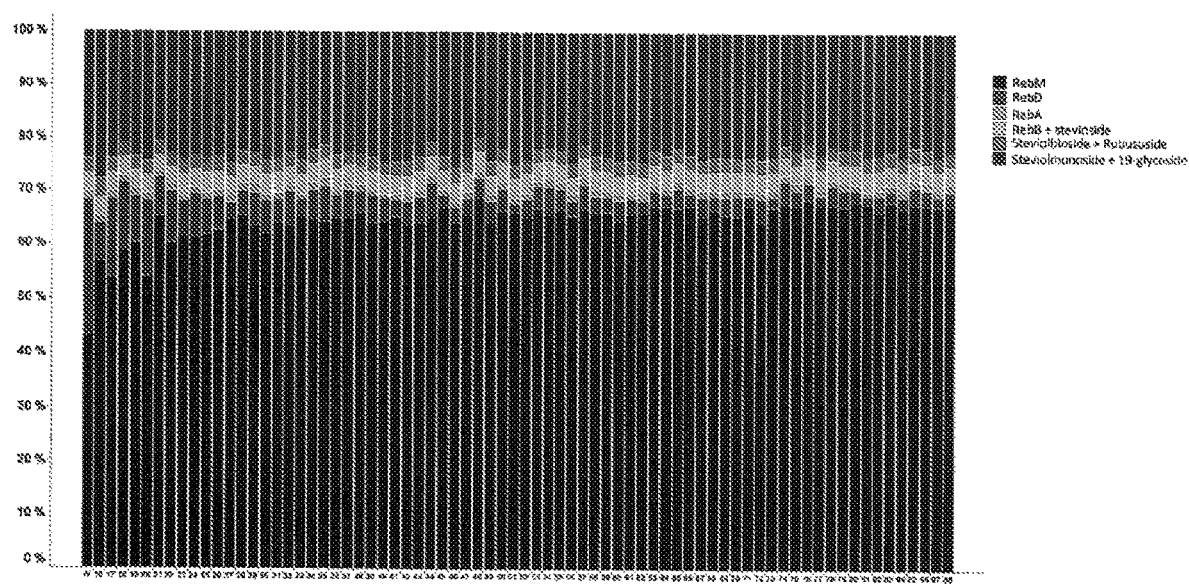
FIG. 14 is a graph showing the relative amounts of various steviol glycosides made in each of several strains expressing variant UGT76G1 enzymes relative to wild-type UGT76G1.

In total, 73 unique combinations of mutations were found that increased RebM titers (FIG. 10), decreased RebD titers (FIG. 11), and increased the ratio of RebM:RebD (FIG. 12). The top combinatorial mutant (number 81) in Strain 2 increased the RebM:RebD ratio by 24 fold over the wild type control (FIG. 12: wt RebM/RebD ratio=1.85 and mutant number 81 RebM/RebD ratio=44.93). The TSG for strains containing a combinatorial UGT76G1 mutant allele (along with a wild type UGT76G1) either was equivalent to, or higher than, the wild type control strain (FIG. 13). Again, the amount of stevioside did not significantly change in the strains with combinatorial a UGT76G1 mutant allele (FIG. 14), confirming that the new UGT76G1 mutant alleles do not interfere with the wild type copy of UGT76G1, they do not interfere with conversion of stevioside to RebA, and they have improved ability to outcompete overexpressed BPT1 for the substrate REbD.

TABLE 5

List of all combinatorial UGT76G1 Mutations that increase RebM titers and/or decrease RebD titers without affecting the total steviol glycosides produced.

| Variant | # | TSG (median) | Fold increase in RebM (median) | Fold decrease in RebD (median) | RebM/RebD (median) | TSG (stdev) | Fold increase RebM (stdev) | Fold decrease in RebD (stdev) | RebM/RebD (stdev) |
|---|---|---|---|---|---|---|---|---|---|
| wild type control | NA | 1 | 1 | 1 | 1.68 | 0.04 | 0.05 | 0.05 | 0.07 |
| H155V, L200M | 16 | 0.91 | 1.18 | 3.98 | 8.04 | 0.05 | 0.07 | 0.2 | 0.25 |
| H155G, L200E | 17 | 1.03 | 1.29 | 1.67 | 3.84 | 0.07 | 0.11 | 0.17 | 0.14 |
| L85H, A125F, H155G, L200M | 18 | 0.95 | 1.29 | 2.06 | 4.54 | 0.09 | 0.12 | 0.18 | 0.13 |
| A125F, H155G, L200K, L379M | 19 | 0.97 | 1.35 | 2.88 | 6.77 | 0.1 | 0.15 | 0.23 | 0.21 |
| L200K, L379Q | 20 | 1.08 | 1.35 | 1.66 | 3.97 | 0.05 | 0.09 | 0.04 | 0.2 |
| A125F, H155T, L200M | 21 | 0.9 | 1.36 | 3.76 | 8.98 | 0.06 | 0.09 | 0.18 | 0.24 |
| L85H, L200M, L379Q | 22 | 0.99 | 1.38 | 2.56 | 6.17 | 0.07 | 0.11 | 0.16 | 0.17 |
| L85H, H155G, L200G, L379M | 23 | 0.97 | 1.38 | 3.9 | 9.56 | 0.17 | 0.21 | 0.39 | 0.75 |
| L85H, A125F, H155V, L200M | 24 | 1 | 1.41 | 3.1 | 7.71 | 0.06 | 0.1 | 0.2 | 0.22 |
| L85H, A125F, H155I, L200C, L379Q | 25 | 1 | 1.42 | 3.75 | 9.29 | 0.07 | 0.11 | 0.25 | 0.13 |
| A125F, H155L, L200E, L379Q | 26 | 1.03 | 1.48 | 3.81 | 9.84 | 0.1 | 0.15 | 0.43 | 0.17 |
| H155T, L200G, L379M | 27 | 1.01 | 1.5 | 7.32 | 19.65 | 0.08 | 0.13 | 0.73 | 0.69 |
| H155L, L200M | 28 | 1.01 | 1.51 | 5.27 | 13.87 | 0.09 | 0.14 | 0.54 | 0.23 |
| H155V, L200C | 29 | 1.03 | 1.51 | 3.91 | 10.17 | 0.06 | 0.1 | 0.21 | 0.18 |
| L85H, H155T, L200G | 30 | 1.07 | 1.52 | 3.75 | 9.91 | 0.09 | 0.13 | 0.3 | 0.15 |
| L85H, H155I, L200C, L379Q | 31 | 1.04 | 1.53 | 5.55 | 14.97 | 0.04 | 0.07 | 0.33 | 0.82 |
| H155I, L200M, L379Q | 32 | 1.05 | 1.54 | 3.74 | 9.98 | 0.03 | 0.04 | 0.13 | 0.43 |
| L85H, A125F, H155T, L200E, L379M | 33 | 1.03 | 1.54 | 7.37 | 19.24 | 0.09 | 0.15 | 0.81 | 0.55 |
| L85H, H155T, L200M | 34 | 1.04 | 1.54 | 4.39 | 11.65 | 0.08 | 0.12 | 0.37 | 0.22 |
| H155V, L200C, L379M | 35 | 1.04 | 1.55 | 3.63 | 9.61 | 0.05 | 0.09 | 0.3 | 0.39 |
| L85H, A125F, L200M, L379M | 36 | 1.05 | 1.55 | 5.43 | 14.58 | 0.06 | 0.09 | 0.42 | 0.48 |
| H155V, L379Q | 37 | 1.05 | 1.56 | 4.29 | 11.51 | 0.06 | 0.1 | 0.36 | 0.5 |
| L85H, L200K, L379M | 38 | 1.03 | 1.56 | 5.96 | 16.1 | 0.07 | 0.11 | 0.42 | 0.32 |
| L85H, A125F, H155L, L200M, L379Q | 39 | 1.06 | 1.56 | 4.58 | 12.63 | 0.06 | 0.11 | 0.29 | 0.5 |
| L85H, A125F, H155I, L200K, L379M | 40 | 1.07 | 1.57 | 5.41 | 14.5 | 0.08 | 0.12 | 0.34 | 0.54 |
| H155I, L379M | 41 | 1.05 | 1.57 | 7.35 | 20.01 | 0.08 | 0.12 | 0.6 | 0.27 |
| L200M, L379M | 42 | 1.08 | 1.57 | 5.26 | 14.32 | 0.08 | 0.12 | 0.33 | 0.31 |
| L85H, H155V, L200G, L379Q | 43 | 1.06 | 1.57 | 4.73 | 12.91 | 0.04 | 0.06 | 0.15 | 0.24 |
| H155T, L200E | 44 | 1.05 | 1.57 | 3.7 | 10.25 | 0.11 | 0.16 | 0.38 | 0.3 |
| H155V, L379M | 45 | 1.03 | 1.59 | 10.97 | 30.67 | 0.06 | 0.1 | 0.7 | 1.15 |
| A125F, H155I, L379M | 46 | 1.08 | 1.59 | 8.09 | 22.69 | 0.07 | 0.11 | 0.49 | 0.4 |
| H155V, L200C, L379Q | 47 | 1.06 | 1.59 | 7.46 | 20.58 | 0.07 | 0.12 | 0.55 | 1.24 |
| L85H, H155G, L200K, L379Q | 48 | 1.01 | 1.59 | 6.61 | 18.47 | 0.11 | 0.17 | 0.78 | 0.31 |
| A125F, H155G, L200M, L379M | 49 | 1.08 | 1.6 | 5.59 | 15.23 | 0.03 | 0.06 | 0.16 | 0.52 |
| H155T, L200E, L379Q | 50 | 1.06 | 1.6 | 5.47 | 15.11 | 0.02 | 0.04 | 0.17 | 0.34 |
| L200K, L379G | 51 | 1.06 | 1.6 | 13.7 | 38.18 | 0.04 | 0.07 | 1.14 | 1.84 |
| L85H, H155L, L200C, L379M | 52 | 1.08 | 1.61 | 7.04 | 19.31 | 0.06 | 0.09 | 0.36 | 0.24 |
| A125F, H155I, L200K, L379M | 53 | 1.06 | 1.62 | 5.78 | 15.99 | 0.06 | 0.09 | 0.36 | 0.34 |
| L85H, H155V, L200M | 54 | 1.08 | 1.63 | 4.44 | 12.47 | 0.03 | 0.04 | 0.19 | 0.62 |
| L85H, H155V, L200E, L379V | 55 | 1.07 | 1.63 | 5.99 | 16.96 | 0.07 | 0.11 | 0.73 | 0.96 |
| L85H, H155V, L200M, L379Q | 56 | 1.09 | 1.64 | 7.83 | 21.83 | 0.07 | 0.11 | 0.83 | 1.23 |
| L85H, L200M, L379M | 57 | 1.07 | 1.64 | 5.01 | 14.08 | 0.05 | 0.08 | 0.25 | 0.22 |
| H155V, L200E, L379M | 58 | 1.08 | 1.64 | 7.19 | 20.43 | 0.08 | 0.12 | 0.9 | 1.14 |

TABLE 5-continued

List of all combinatorial UGT76G1 Mutations that increase RebM titers and/or decrease RebD titers without affecting the total steviol glycosides produced.

| Variant | # | TSG (median) | Fold increase in RebM (median) | Fold decrease in RebD (median) | RebM/RebD (median) | TSG (stdev) | Fold increase RebM (stdev) | Fold decrease in RebD (stdev) | RebM/RebD (stdev) |
|---|---|---|---|---|---|---|---|---|---|
| L85H, H155I, L200M, L379M | 59 | 1.09 | 1.64 | 8.15 | 23.26 | 0.04 | 0.07 | 0.64 | 1.26 |
| L85H, H155L, L200M, L379Q | 60 | 1.12 | 1.65 | 5.65 | 16.11 | 0.07 | 0.11 | 0.4 | 0.39 |
| L85H, A125F, H155T, L200C, L379M | 61 | 1.09 | 1.65 | 7.68 | 21.31 | 0.05 | 0.09 | 0.63 | 1.23 |
| L85H, A125F, H155L, L200K, L379M | 62 | 1.09 | 1.65 | 10.4 | 29.18 | 0.04 | 0.06 | 0.49 | 0.7 |
| V20L, L85M, A125P | 63 | 1.07 | 1.66 | 7.73 | 22.25 | 0.06 | 0.1 | 0.72 | 1.61 |
| L85H, H155L, L200K, L379M | 64 | 1.08 | 1.66 | 11.33 | 33.36 | 0.05 | 0.07 | 1.09 | 2.84 |
| L85H, H155V, L200C, L379Q | 65 | 1.08 | 1.66 | 6.32 | 18.02 | 0.06 | 0.1 | 0.7 | 1.06 |
| H155I, L200K, L379M | 66 | 1.07 | 1.66 | 9.96 | 28.17 | 0.08 | 0.14 | 1.19 | 1.09 |
| L85H, H155L, L200C | 67 | 1.11 | 1.67 | 6.25 | 17.95 | 0.04 | 0.05 | 0.41 | 0.71 |
| L85H, A125F, H155L, L379M | 68 | 1.08 | 1.67 | 8.43 | 24.36 | 0.04 | 0.07 | 0.58 | 0.87 |
| L85H, H155I, L200E, L379M | 69 | 1.11 | 1.67 | 6.75 | 19.59 | 0.02 | 0.04 | 0.57 | 1.87 |
| L85H, A125F, H155G, L200M, L379M | 70 | 1.11 | 1.67 | 5.73 | 16.52 | 0.05 | 0.07 | 0.25 | 0.17 |
| L85H, H155L, L200E, L379M | 71 | 1.08 | 1.67 | 12.28 | 34.48 | 0.08 | 0.12 | 1.19 | 2.32 |
| H155L, L200C | 72 | 1.14 | 1.67 | 4.78 | 13.94 | 0.05 | 0.07 | 0.33 | 0.55 |
| L85H, H155L, L200C, L379E | 73 | 1.09 | 1.67 | 11.5 | 32.42 | 0.07 | 0.11 | 1.05 | 1.25 |
| L85H, H155V, L200K, L379Q | 74 | 1.07 | 1.67 | 5.56 | 16.16 | 0.02 | 0.03 | 0.09 | 0.35 |
| H155T, L200K, L379M | 75 | 1.09 | 1.68 | 7.83 | 22.43 | 0.07 | 0.12 | 0.61 | 0.42 |
| H155V, L200G, L379M | 76 | 1.08 | 1.69 | 7.92 | 23.16 | 0.05 | 0.09 | 0.53 | 0.55 |
| L85H, A125F, H155V, L200M, L379M | 77 | 1.09 | 1.69 | 11.57 | 33.68 | 0.09 | 0.14 | 0.83 | 0.72 |
| A125F, H155G, L200C, L379M | 78 | 1.09 | 1.69 | 6.16 | 17.66 | 0.07 | 0.13 | 0.47 | 0.91 |
| A125F, H155L, L379M | 79 | 1.11 | 1.7 | 6.74 | 19.79 | 0.03 | 0.07 | 0.19 | 0.43 |
| L85H, H155L, L200G, L379M | 80 | 1.09 | 1.71 | 10.19 | 30.01 | 0.07 | 0.12 | 0.83 | 1.14 |
| L85H, H155L, L200E, L379Q | 81 | 1.11 | 1.72 | 15.14 | 44.93 | 0.07 | 0.13 | 1.14 | 2.82 |
| H155G, L200E, L379M | 82 | 1.14 | 1.73 | 6.85 | 20.33 | 0.04 | 0.06 | 0.33 | 0.58 |
| H155L, L200C, L379Q | 83 | 1.11 | 1.73 | 10.62 | 31.99 | 0.05 | 0.09 | 0.71 | 2.5 |
| L85H, H155V, L379M | 84 | 1.13 | 1.74 | 10.86 | 32.94 | 0.08 | 0.11 | 1.23 | 2.76 |
| L85H, A125F, H155I, L200C, L379M | 85 | 1.12 | 1.74 | 6.61 | 20 | 0.07 | 0.1 | 0.41 | 1.03 |
| H155G, L200C, L379M | 86 | 1.11 | 1.74 | 7.07 | 21.59 | 0.04 | 0.07 | 0.54 | 0.75 |
| A125F, H155V, L200M, L379M | 87 | 1.15 | 1.78 | 10.97 | 32.86 | 0.07 | 0.11 | 0.9 | 1.42 |
| H155L, L200E | 88 | 1.17 | 1.82 | 7.58 | 24 | 0.05 | 0.1 | 0.41 | 0.65 |

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

```
                       SEQUENCE LISTING

Sequence total quantity: 16
SEQ ID NO: 1           moltype = AA  length = 458
FEATURE                Location/Qualifiers
source                 1..458
                       mol_type = protein
                       organism = Stevia rebaudiana
SEQUENCE: 1
MENKTETTVR RRRRIILFPV PFQGHINPIL QLANVLYSKG FSITIFHTNF NKPKTSNYPH   60
FTFRFILDND PQDERISNLP THGPLAGMRI PIINEHGADE LRRELELLML ASEEDEEVSC  120
LITDALWYFA QSVADSLNLR RLVLMTSSLF NFHAHVSLPQ FDELGYLDPD DKTRLEEQAS  180
GFPMLKVKDI KSAYSNWQIL KEILGKMIKQ TKASSGVIWN SFKELEESEL ETVIREIPAP  240
SFLIPLPKHL TASSSSLLDH DRTVFQWLDQ QPPSSVLYVS FGSTSEVDEK DFLEIARGLV  300
DSKQSFLWVV RPGFVKGSTW VEPLPDGFLG ERGRIVKWVP QQEVLAHGAI GAFWTHSGWN  360
STLESVCEGV PMIFSDFGLD QPLNARYMSD VLKVGVYLEN GWERGEIANA IRRVMVDEEG  420
EYIRQNARVL KQKADVSLMK GGSSYESLES LVSYISSL                         458

SEQ ID NO: 2           moltype = DNA  length = 1377
FEATURE                Location/Qualifiers
source                 1..1377
                       mol_type = genomic DNA
                       organism = Stevia rebaudiana
SEQUENCE: 2
atggaaaaca agaccgagac tactgttaga agaagaagaa gaattatttt gttcccagtt   60
ccattccaag gtcatatcaa ccctattttg caattggcta atgtcttgta ctccaaaggt  120
ttctctatca ctatcttcca cactaacttc aacaagccaa agacttctaa ctatccacac  180
ttcactttcc gttttatttt ggataacgac ccacaagatg aaagaatttc taacttgcca  240
```

```
                                        -continued
acccacggtc cattggccgg tatgcgtatc ccaatcatta atgaacatgg tgccgacgaa    300
ttgagacgtg aattggaatt attgatgttg cttccgaagg aagacgaaga agtttcttgt    360
ttgatcaccg atgccttgtg gtactttgcc caatccgtcg ccgattcttt gaacttgaga    420
cgtttagttt tgatgacctc ttccttgttc aattttcacg ctcacgtttc cttgccacaa    480
ttcgacgaat tgggttactt agacccagac gacaagacta gattggaaga acaagcttcc    540
ggtttcccaa tgttaaaggt taaggacatt aagtccgctt actccaactg gcaaatttta    600
aaagaaattt taggtaaaat gattaagcaa accaaggctc ttccggtgt catttggaac     660
tctttcaagg aattggaaga atctgaattg gaaactgtta ttagaaaat tccagctcca     720
tctttcttga ttccattacc aaaacacttg accgcttcct cctcttcctt gttagatcat    780
gacagaaccg tctttcaatg gttgaccaa caaccacctt cttctgtttt gtatgtctct     840
ttcggttcca cttccgaagt tgacgaaaaa gacttcttgg aaatcgccag aggttttggtc   900
gactctaagc aatccttctt gtgggtcgtt agaccaggtt cgtcaaagg ttctacctgg     960
gttgaaccat tgccagatgg tttctttggg gaaagaggtc gtatcgttaa atgggttcca   1020
caacaagaag ttttagctca cggtgctatc ggtgccttct ggacccactc tggttggaac   1080
tctactttgg aatctgtttg tgaaggtgtc cctatgattt tctctgactt cggtttagac   1140
caaccattaa acgctagata catgtctgat gtcttaaagg ttggtgtcta tttggagaac   1200
ggttgggaaa gaggtgaaat tgctaatgct attagaagag tcatggtcga cgaagaaggt   1260
gagtacatta gacaaaatgc tagagtcttg aagcaaaagg ctgatgtctc tttgatgaag   1320
ggtggttcct cctacgagtc cttggaatcc ttggtttct atatctcctc cttataa      1377

SEQ ID NO: 3                moltype = AA  length = 320
FEATURE                     Location/Qualifiers
source                      1..320
                            mol_type = protein
                            organism = Blakeslea trispora
SEQUENCE: 3
MLTSSKSIES FPKNVQPYGK HYQNGLEPVG KSQEDILLEP FHYLCSNPGK DVRTKMIEAF     60
NAWLKVPKDD LIVITRVIEM LHSASLLIDD VEDDSVLRRG VPAAHHIYGT PQTINCANYV    120
YFLALKEIAK LNKPNMITIY TDELINLHRG QGMELFWRDT LTCPTEKEFL DMVNDKTGGL    180
LRLAVKLMQE ASQSGTDYTG LVSKIGIHFQ VRDDYMNLQS KNYADNKGFC EDLTEGKFSF    240
PIIHSIRSDP SNRQLLNILK QRSSSIELKQ FALQLLENTN TFQYCRDFLR VLEKEAREEI    300
KLLGGNIMLE KIMDVLSVNE                                                320

SEQ ID NO: 4                moltype = AA  length = 736
FEATURE                     Location/Qualifiers
source                      1..736
                            mol_type = protein
                            organism = Oryza sativa
SEQUENCE: 4
MEHARPPQGG DDDVAASTSE LPYMIESIKS KLRAARNSLG ETTVSAYDTA WIALVNRLDG     60
GGERSPQFPE AIDWIARNQL PDGSWGDAGM FIVQDRLINT LGCVVALATW GVHEEQRARG    120
LAYIQDNLWR LGEDDEEWMM VGFEITFPVL LEKAKNLGLD INYDDPALQD IYAKRQLKLA    180
KIPREALHAR PTTLLHSLEG MENLDWERLL QFKCPAGSLH SSPAASAYAL SETGDKELLE    240
YLETAINNFD GGAPCTYPVD NFDRLWSVDR LRRLGISRYF TSEIEEYLEY AYRHLSPDGM    300
SYGGLCPVKD IDDTAMAFRL LRLHGYNVSS SVFNHFEKDG EYFCFAGQSS QSLTAMYNSY    360
RASQIVFPGD DDGLEQLRAY CRAFLEERRA TGNLRDKWVI ANGLPSEVEY ALDFPWKASL    420
PRVETRVYLE QYGASEDAWI GKGLYRMTLV NNDLYLEAAK ADFTNFQRLS RLEWLSLKRW    480
YIRNNLQAHG VTEQSVLRAY FLAAANIFEP NRAAERLGWA RTAILAEAIA SHLRQYSANG    540
AADGMTERLI SGLASHDWDW RESNDSAARS LLYALDELID LHAFGNASDS LREAWKQWLM    600
SWTNESQGST GGDTALLLVR TIEICSGRHG SAEQSLKNSE DYARLEQIAS SMCSKLATKI    660
LAQNGGSMDN VEGIDQEVDV EMKELIQRVY GSSSNDVSSV TRQTFLDVVK SFCYVAHCSP    720
ETIDGHISKV LFEDVN                                                    736

SEQ ID NO: 5                moltype = AA  length = 757
FEATURE                     Location/Qualifiers
source                      1..757
                            mol_type = protein
                            organism = Picea glauca
SEQUENCE: 5
MKREQYTILN EKESMAEELI LRIKRMFSEI ENTQTSASAY DTAWVAMVPS LDSSQQPQFP     60
QCLSWIIDNQ LLDGSWGIPY LIIKDRLCHT LACVIALRKW NAGNQNVETG LRFLRENIEG    120
IVHEDEYTPI GFQIIFPAML EEARGLGLEL PYDLTPIKLM LTHREKIMKG KAIDHMHEYD    180
SSLIYTVEGI HKIVDWNKVL KHQNKDGSLF NSPSATACAL MHTRKSNCLE YLSSMLQKLG    240
NGVPSVYPIN LYARISMIDR LQRLGLARHF RNEIIHALDD IYRYWMQRET SREGKSLTPD    300
IVSTSIAFML LRLHGYDVPA DVFCCYDLHS IEQSGEAVTA MLSLYRASQI MFPGETILEE    360
IKTVSRKYLD KRKENGGIYD HNIVMKDLRG EVEYALSVPW YASLERIENR RYIDQYGVND    420
TWIAKTSYKI PCISNDLFLA LAKQDYNICQ AIQQKELREL ERWFADNKFS HLNFARQKLI    480
YCYFSAAATL FSPELSAARV VWAKNGVITT VDDDFFDVGG SSEEIHSFVE AVRVWDEAAT    540
DGLSENVQIL FSALYNTVDE IVQQAFVFQG RDISIHLREI WYRLVNSMMT EAQWARTHCL    600
PSMHEYMENA EPSIALEPIV LSSLYFVGPK LSEEIICHPE YYNLMHLLNI CGRLLNDIQG    660
CKREAHQGKL NSVTLYMEEN SGTTMEDAIV YLRKTIDESR QLLLKEVLRP SIVPRECKQL    720
HWNMMRILQL FYLKNDGFTS PTEMLGYVNA VIVDPIL                             757

SEQ ID NO: 6                moltype = AA  length = 499
FEATURE                     Location/Qualifiers
source                      1..499
                            mol_type = protein
                            organism = Pisum sativum
SEQUENCE: 6
```

```
MDTLTLSLGF LSLFLFLFLL KRSTHKHSKL SHVPVVPGLP VIGNLLQLKE KKPHKTFTKM   60
AQKYGPIFSI KAGSSKIIVL NTAHLAKEAM VTRYSSISKR KLSTALTILT SDKCMVAMSD  120
YNDFHKMVKK HILASVLGAN AQKRLRFHRE VMMENMSSKF NEHVKTLSDS AVDFRKIFVS  180
ELFGLALKQA LGSDIESIYV EGLTATLSRE DLYNTLVVDF MEGAIEVDWR DFFPYLKWIP  240
NKSFEKKIRR VDRQRKIIMK ALINEQKKRL TSGKELDCYY DYLVSEAKEV TEEQMIMLLW  300
EPIIETSDTT LVTTEWAMYE LAKDKNRQDR LYEELLNVCG HEKVTDEELS KLPYLGAVFH  360
ETLRKHSPVP IVPLRYVDED TELGGYHIPA GSEIAINIYG CNMDSNLWEN PDQWIPERFL  420
DEKYAQADLY KTMAFGGGKR VCAGSLQAML IACTAIGRLV QEFEWELGHG EEENVDTMGL  480
TTHRLHPLQV KLKPRNRIY                                              499

SEQ ID NO: 7              moltype = AA  length = 711
FEATURE                   Location/Qualifiers
source                    1..711
                          mol_type = protein
                          organism = Arabidopsis thaliana
SEQUENCE: 7
MSSSSSSSTS MIDLMAAIIK GEPVIVSDPA NASAYESVAA ELSSMLIENR QFAMIVTTSI   60
AVLIGCIVML VWRRSGSGNS KRVEPLKPLV IKPREEEIDD GRKKVTIFFG TQTGTAEGFA  120
KALGEEAKAR YEKTRFKIVD LDDYAADDDE YEEKLKKEDV AFFFLATYGD GEPTDNAARF  180
YKWFTEGNDR GEWLKNLKYG VFGLGNRQYE HFNKVAKVVD DILVEQGAQR LVQVGLGDDD  240
QCIEDDFTAW REALWPELDT ILREEGDTAV ATPYTAAVLE YRVSIHDSED AKFNDINMAN  300
GNGYTVFDAQ HPYKANVAVK RELHTPESDR SCIHLEFDIA GSGLTYETGD HVGVLCDNLS  360
ETVDEALRLL DMSPDTYFSL HAEKEDGTPI SSSLPPPFPP CNLRTALTRY ACLLSSPKKS  420
ALVALAAHAS DPTEAERLKH LASPAGKDEY SKWVVESQRS LLEVMAEFPS AKPPLGVFFA  480
GVAPRLQPRF YSISSSPKIA ETRIHVTCAL VYEKMPTGRI HKGVCSTWMK NAVPYEKSEN  540
CSSAPIFVRQ SNFKLPSDSK VPIIMIGPGT GLAPFRGFLQ ERALVESGV ELGPSVLFFG   600
CRNRRMDFIY EEELQRFVES GALAELSVAF SREGPTKEYV QHKMMDKASD IWNMISQGAY  660
LYVCGDAKGM ARDVHRSLHT IAQEQGSMDS TKAEGFVKNL QTSGRYLRDV W          711

SEQ ID NO: 8              moltype = AA  length = 500
FEATURE                   Location/Qualifiers
source                    1..500
                          mol_type = protein
                          organism = Stevia rebaudiana
SEQUENCE: 8
MEASYLYISI LLLLASYLFT TQLRRKSANL PPTVFPSIPI IGHLYLLKKP LYRTLAKIAA   60
KYGPILQLQL GYRRVLVISS PSAAEECFTN NDVIFANRPK TLFGKIVGGT SLGSLSYGDQ  120
WRNLRRVASI EILSVHRLNE FHDIRVDENR LLIRKLRSSS SPVTLITVFY ALTLNVIMRM  180
ISGKRYFDSG DRELEEEGKR FREILDETLL LAGASNVGDY LPILNWLGVK SLEKKLIALQ  240
KKRDDFFQGL IEQVRKSRGA KVGKGRKTMI ELLLSLQESE PEYYTDAMIR SFVLGLLAAG  300
SDTSAGTMEW AMSLLVNHPH VLKKAQAEID RVIGNNRLID ESDIGNIPYI GCIINETLRL  360
YPAGPLLFPH ESSADCVISG YNIPRGTMLI VNQWAIHHDP KVWDDPETFK PERFQGLEGT  420
RDGFKLMPFG SGRRGCPGEG LAIRLLGMTL GSVIQCFDWE RVGDEMVDMT EGLGVTLPKA  480
VPLVAKCKPR SEMTNLLSEL                                             500

SEQ ID NO: 9              moltype = AA  length = 481
FEATURE                   Location/Qualifiers
source                    1..481
                          mol_type = protein
                          organism = Stevia rebaudiana
SEQUENCE: 9
MDAMATTEKK PHVIFIPFPA QSHIKAMLKL AQLLHHKGLQ ITFVNTDFIH NQFLESSGPH   60
CLDGAPGFRF ETIPDGVSHS PEASIPIRES LLRSIETNFL DRFIDLVTKL PDPPTCIISD  120
GFLSVFTIDA AKKLGIPVMM YWTLAACGFM GFYHIHSLIE KGFAPLKDAS YLTNGYLDTV  180
IDWVPGMEGI RLKDFPLDWS TDLNDKVLMF TTEAPQRSHL VSHHIFHTFD ELEPSIIKTL  240
SLRYNHIYTI GPLQLLLDQI PEEKKQTGIT SLHGYSLVKE EPECFQWLQS KEPNSVVYVN  300
FGSTTVMSLE DMTEFGWGLA NSNHYFLWII RSNLVIGENA VLPPELEEHI KKRGFIASWC  360
SQEKVLKHPS VGGFLTHCGW GSTIESLSAG VPMICWPYSW DQLTNCRYIC KEWEVGLEMG  420
TKVKRDEVKR LVQELMGEGG HKMRNKAKDW KEKARIAIAP NGSSSLNIDK MVKEITVLAR  480
N                                                                 481

SEQ ID NO: 10             moltype = AA  length = 460
FEATURE                   Location/Qualifiers
source                    1..460
                          mol_type = protein
                          organism = Stevia rebaudiana
SEQUENCE: 10
MAEQQKIKKS PHVLLIPFPL QGHINPFIQF GKRLISKGVK TTLVTTIHTL NSTLNHSNTT   60
TTSIEIQAIS DGCDEGGFMS AGESYLETFK QVGSKSLADL IKKLQSEGTT IDAIIYDSMT  120
EWVLDVAIEF GIDGGSFFTQ ACVVNSLYYH VHKGLISLPL GETVSVPGFP VLQRWETPLI  180
LQNHEQIQSP WSQMLFGQFA NIDQARWVFT NSFYKLEEEV IEWTRKIWNL KVIGPTLPSM  240
YLDKRLDDDK DNGFNLYKAN HHECMNWLDD KPKESVVYVA FGSLVKHGPE QVEEITRALI  300
DSDVNFLWVI KHKEEGKLPE NLSEVIKTGK GLIVAWCKQL DVLAHESVGC FVTHCGFNST  360
LEAISLGVPV VAMPQFSDQT TNAKLLDEIL GVGVRVKADE NGIVRRGNLA SCIKMIMEEE  420
RGVIIRKNAV KWKDLAKVAV HEGGSSDNDI VEFVSELIKA                       460

SEQ ID NO: 11             moltype = AA  length = 485
FEATURE                   Location/Qualifiers
source                    1..485
```

```
                            mol_type = protein
                            organism = Stevia rebaudiana
SEQUENCE: 11
MYNVTYHQNS  KAMATSDSIV  DDRKQLHVAT  FPWLAFGHIL  PYLQLSKLIA  EKGHKVSFLS   60
TTRNIQRLSS  HISPLINVVQ  LTLPRVQELP  EDAEATTLVH  PEDIPYLKKA  SDGLQPEVTR  120
FLEQHSPDWI  IYDYTHYWLP  SIAASLGISR  AHFSVTTPWA  IAYMGPSADA  MINGSDGRTT  180
VEDLTTPPKW  FPFPTKVCWR  KHDLARLVPY  KAPGISDGYR  MGLVLKGSDC  LLSKCYHEFG  240
TQWLPLLETL  HQVPVPVGL   LPPEIPGDEK  DETWVSIKKW  LDGKQKGSVV  YVALGSEVLV  300
SQTEVVELAL  GLELSGLPFV  WAYRKPKGPA  KSDSVELPDG  FVERTRDRGL  VWTSWAPQLR  360
ILSHESVCGF  LTHCGSGSIV  EGLMFGHPLI  MLPIFGDQPL  NARLLEDKQV  GIEIPRNEED  420
GCLTKESVAR  SLRSVVVEKE  GEIYKANARE  LSKIYNDTKV  EKEYVSQFVD  YLEKNARAVA  480
IDHES                                                                  485

SEQ ID NO: 12           moltype = AA   length = 436
FEATURE                 Location/Qualifiers
REGION                  1..436
                        note = Synthetic: UGT40087
source                  1..436
                        mol_type = protein
                        organism = synthetic construct
SEQUENCE: 12
MDASDSSPLH  IVIFPWLAFG  HMLASLELAE  RLAARGHRVS  FVSTPRNISR  LRPVPPALAP   60
LIDFVALPLP  RVDGLPDGAE  ATSDIPPGKT  ELHLKALDGL  AAPFAAFLDA  ACADGSTNKV  120
DWLFLDNFQY  WAAAAADHK   IPCALNLTFA  ASTSAEYGVP  RVEPPVDGST  ASILQRFVLT  180
LEKCQFVIQR  ACFELEPEPL  PLLSDIFGKP  VIPYGLVPPC  PPAEGHKREH  GNAALSWLDK  240
QQPESVLFIA  LGSEPPVTVE  QLHEIALGLE  LAGTTFLWAL  KKPNGLLLEA  DGDILPPGFE  300
ERTRDRGLVA  MGWVPQPIIL  AHSSVGAFLT  HGGWASTIEG  VMSGHPMLFL  TFLDEQRINA  360
QLIERKKAGL  RVPRREKDGS  YDRQGIAGAI  RAVMCEEESK  SVFAANAKKM  QEIVSDRNCQ  420
EKYIDELIQR  LGSFEK                                                     436

SEQ ID NO: 13           moltype = AA   length = 523
FEATURE                 Location/Qualifiers
REGION                  1..523
                        note = Synthetic: KAH
source                  1..523
                        mol_type = protein
                        organism = synthetic construct
SEQUENCE: 13
MEVTVASSVA  LSLVFISIVV  RWAWSVVNWV  WFKPKKLERF  LREQGLKGNS  YRFLYGDMKE   60
NSILLKQARS  KPMNLSTSHD  IAPQVTPFVD  QTVKAYGKNS  FNWVGPIPRV  NIMNPEDLKD  120
VLTKNVDFVK  PISNPLIKLL  ATGIAIYEGE  KWTKHRRIIN  PTFHSERLKR  MLPSFHQSCN  180
EMVKEWESLV  SKEGSSCELD  VWPFLENMSA  DVISRTAFGT  SYKKGQKIFE  LLREQVIYVT  240
KGFQSFYIPG  WRFLPTKMNK  RMNEINEEIK  GLIRGIIIDR  EQIIKAGEET  NDDLLGALME  300
SNLKDIREHG  KNNKNVGMSI  EDVIQECKLF  YFAGQETTSV  LLAWTMVLLG  QNQNWQDRAR  360
QEVLQVFGSS  KPDFDGLAHL  KVVTMILLEV  LRLYPPVIEL  IRTIHKKTQL  GKLSLPEGVE  420
VRLPTLLIHH  DKELWGDDAN  QFNPERFSEG  VSKATKNRLS  FFPFGAGPRI  CIGQNFSMME  480
AKLALALILQ  HFTFELSPSH  AHAPSHRITL  QPQYGVRIIL  HRR                    523

SEQ ID NO: 14           moltype = AA   length = 525
FEATURE                 Location/Qualifiers
source                  1..525
                        mol_type = protein
                        organism = Arabidopsis thaliana
SEQUENCE: 14
MESLVVHTVN  AIWCIVIVGI  FSVGYHVYGR  AVVEQWRMRR  SLKLQGVKGP  PPSIFNGNVS   60
EMQRIQSEAK  HCSGDNIISH  DYSSSLFPHF  DHWRKQYGRI  YTYSTGLKQH  LYINHPEMVK  120
ELSQTNTLNL  GRITHITKRL  NPILGNGIIT  SNGPHWAHQR  RIIAYEFTHD  KIKGMVGLMV  180
ESAMPMLNKW  EEMVKRGGEM  GCDIRVDEDL  KDVSADVIAK  ACFGSSFSKG  KAIFSMIRDL  240
LTAITKRSVL  FRFNGPTDMV  FGSKKHGDVD  IDALEMELES  JIWETVKERE  IECKDTHKKD  300
LMQLILEGAM  RSCDGNLWDK  SAYRRFVVDN  CKSIYFAGHD  STAVSVSWCL  MLLALNPSWQ  360
VKIRDEILSS  CKNGIPDAES  IPNLKTVTMV  IQETMRLYPP  APIVGREASK  DIRLGDVVP   420
KGVCIWTLIP  ALHRDPEIWG  PDANDFKPER  FSEGISKACK  YPQSYIPFGL  GPRTCVGKNF  480
GMMEVKVLVS  LIVSKFSFTL  SPTYQHSPSH  KLLVEPQHGV  VIRVV                  525

SEQ ID NO: 15           moltype = AA   length = 1559
FEATURE                 Location/Qualifiers
source                  1..1559
                        mol_type = protein
                        organism = Saccharomyces cerevisiae
SEQUENCE: 15
MSSLEVVDGC  PYGYRPYPDS  GTNALNPCFI  SVISAWQAVF  FLLIGSYQLW  KLYKNNKVPP   60
RFKNFPTLPS  KINSRHLTHL  TNVCFQSTLI  ICELALVSQS  SDRVYPFILK  KALYLNLLFN  120
LGISLPTQYL  AYFKSTFSMG  NQLFYYMFQI  LLQLFLILQR  YHGSSNERL   TVISGQTAMI  180
LEVLLLFNSV  AIFIYDLCIF  EPINELSEYY  KKNGWYPPVH  VLSYITFIWM  NKLIVETYRN  240
KKIKDPNQLP  LPPVDLNIKS  ISKEFKANWE  LEKWLNRNSL  WRAIWKSFGR  TISVAMLYET  300
TSDLLSVVQP  QFLRIPIDGL  NPETSSKYPP  LNGVFIALTL  FVISVVSVFL  TNQFYIGIFE  360
AGLGIRGSLA  SLVVYQKSLRL  TLAERNEKST  GDILNLMSVD  VLRIQRFFEN  AQTIIGAPIQ  420
IIVVLTSLYW  LLGKAVIGGL  VTMAIMMPIN  AFLSRKVKKL  SKTQMKYKDM  RIKTITELLN  480
AIKSIKLYAW  EEPMMARLNH  VRNDMELKNF  RKIGIVSNLI  YFAWNCVPLM  VTCSTFGLFS  540
```

```
LFSDSPLSPA  IVFPSLSLFN  ILNSAIYSVP  SMINTIIETS  VSMERLKSFL  LSDEIDDSFI   600
ERIDPSADER  ALPAIEMNNI  TFLWKSKEVL  TSSQSGDNLR  TDEESIIGSS  QIALKNIDHF   660
EAKRGDLVCV  VGRVGAGKST  FLKAILGQLP  CMSGSRDSIP  PKLIIRSSSV  AYCSQESWIM   720
NASVRENILF  GHKFDQDYYD  LTIKACQLLP  DLKILPDGDE  TLVGEKGISL  SGGQKARLSL   780
ARAVYSRADI  YLLDDILSAV  DAEVSKNIIE  YVLIGKTALL  KNKTIILTTN  TVSILKHSQM   840
IYALENGEIV  EQGNYEDVMN  RKNNTSKLKK  LLEEFDSPID  NGNESDVQTE  HRSESEVDEP   900
LQLKVTESET  EDEVVTESEL  ELIKANSRRA  SLATLRPRPF  VGAQLDSVKK  TAQKAEKTEV   960
GRVKTKIYLA  YIKACGVLGV  VLFFLFMILT  RVFDLAENFW  LKYWSESNEK  NGSNERVWMF  1020
VGVYSLIGVA  SAAFNNLRSI  MMLLYCSIRG  SKKLHESMAK  SVIRSPMTFF  ETTPVGRIIN  1080
RFSSDMDAVD  SNLQYIFSFF  FKSILTYLVT  VILVGYNMPW  FLVFNMFLVV  IYIYYQTFYI  1140
VLSRELKRLI  SISYSPIMSL  MSESLNGYSI  IDAYDHFERF  IYLNYEKIQY  NVDFVFNFRS  1200
TNRWLSVRLQ  TIGATIVLAT  AILALATMNT  KRQLSSGMVG  LLMSYSLEVT  GSLTWIVRTT  1260
VTIETNIVSV  ERIVEYCELP  PEAQSINPEK  RPDENWPSKG  GIEFKNYSTK  YRENLDPVLN  1320
NINVKIEPCE  KVGIVGRTGA  GKSTLSLALF  RILEPTEGKI  IIDGIDISDI  GLFDLRSHLA  1380
IIPQDAQAFE  GTVKTNLDPF  NRYSEDELKR  AVEQAHLKPH  LEKMLHSKPR  GDDSNEEDGN  1440
VNDILDVKIN  ENGSNLSVGQ  RQLLCLARAL  LNRSKILVLD  EATASVDMET  DKIIQDTIRR  1500
EFKDRTILTI  AHRIDTVLDS  DKIIVLDQGS  VREFDSPSKL  LSDKTSIFYS  LCEKGGYLK   1559

SEQ ID NO: 16          moltype = AA  length = 1381
FEATURE                Location/Qualifiers
source                 1..1381
                       mol_type = protein
                       organism = Cyberlindnera jadinii
SEQUENCE: 16
MTSPGSEKCT  PRSDEDLERS  EPQLQRRLLT  PFLLSKKVPP  IPKEDERKPY  PYLKTNPLSQ    60
ILFWWLNPLL  RVGYKRTLDP  NDFYYLEHSQ  DIETTYSNYE  MHLARILEKD  RAKARAKDPT   120
LTDEDLKNRE  YPKNAVIKAL  FLTFKWKYLW  SIFLKLLSDI  VLVLNPLLSK  ALINFVDEKM   180
YNPDMSVGRG  VGYAIGVTFM  LGTSGILINH  FLYLSLTVGA  HCKAVLTTAI  MNKSFRASAK   240
SKHEYPSGRV  TSLMSTDLAR  IDLAIGFQPF  AITVPVPIGV  AIALLIVNIG  VSALAGIAVF   300
LVCIVVISAS  SKSLLKMRKG  ANQYTDARIS  YMREILQNMR  IIKFYSWEDA  YEKSVVTERN   360
SEMSIILKMQ  SIRNFLLALS  LSLPAIISMV  AFLVLYGVSN  DKNPGNIFSS  ISLFSVLAQQ   420
TMMLPMALAT  GADAKIGLER  LRQYLQSGDI  EKEYEDHEKP  GDRDVVLPDN  VAVELNNASF   480
IWEKFDDADD  NDGNSEKTKE  VVVTSKSSLT  DSSHIDKSTD  SADGEYIKSV  FEGFNNINLT   540
IKKGEFVIIT  GPIGSGKSSL  LVALAGFMKK  TSGTLGVNGT  MLLCGQPWVQ  NCTVRDNILF   600
GLEYDEARYD  RVVEVCALGD  DLKMFTAGDQ  TEIGERGITL  SGGQKARINL  ARAVYANKDI   660
ILLDDVLSAV  DARVGKLIVD  DCLTSFLGDK  TRILATHQLS  LIEAADRVIY  LNGDGTIHIG   720
TVQELLESNE  GFLKLMEFSR  KSESEDEEDV  EAANEKDVSL  QKAVSVVQEQ  DAHAGVLIGQ   780
EERAVNGIEW  DIYKEYLHEG  RGKLGIFAIP  TIIMLLVLDV  FTSIFVNVWL  SFWISHKFKA   840
RSDGFYIGLY  VMFVILSVIW  ITAEFVVMGY  FSSTAARRLN  LKAMKRVLHT  PMHFLDVTPM   900
GRILNRFTKD  TDVLDNEIGE  QARMFLHPAA  YVIGVLILCI  IYIPWFAIAI  PPLAILFTFI   960
TNFYIASSRE  VKRIEAIQRS  LVYNNFNEVL  NGLQTLKAYN  ATSRFMEKNK  RLLNRMNEAY  1020
LLVIANQRWI  SVNLDLVSCC  FVFLISMLSV  FRVFDINASS  VGLVVTSVLQ  IGGLMSLIMR  1080
AYTTVENEMN  SVERLCHYAN  KLEQEAPYIM  NETKPRPTWP  EHGAIEFKHA  SMRYREGLPL  1140
VLKDLTISVK  GGEKIGICGR  TGAGKSTIMN  ALYRLTELAE  GSITIDGVEI  SQLGLYDLRS  1200
KLAIIPQDPV  LFRGTIRKNL  DPFGQNDDET  LWDALRRSGL  VEGSILNTIK  SQSKDDPNFH  1260
KFHLDQTVED  EGANFSLGER  QLIALARALV  RNSKILILDE  ATSSVDYETD  SKIQKTISTE  1320
FSHCTILCIA  HRLKTILTYD  RILVLEKGEV  EEFDTPRVLY  SKNGVFRQMC  ERSEITSADF  1380
V                                                                      1381
```

What is claimed:

1. A variant UDP-glycosyltransferase polypeptide comprising the amino acid sequence of SEQ ID NO: 1 with one or more amino acid substitutions, wherein the variant UDP-glycosyltransferase polypeptide produces a higher ratio of RebM/RebD compared to the UDP-glycosyltransferase polypeptide of SEQ ID NO: 1, and wherein the one or more amino acid substitutions are selected from the group consisting of (L85H); (L200G); (L379Q); (H155I); (H155V); (L200K); (V20G); (L200C); (A125F); (H155G); (H155T); (H155L); (L200E); (L200M); and (L379M).

2. A variant UDP-glycosyltransferase polypeptide comprising the amino acid sequence of SEQ ID NO:1 with two or more amino acid substitutions, wherein the variant UDP-glycosyltransferase polypeptide produces a higher ratio of RebM/RebD compared to the UDP-glycosyltransferase polypeptide of SEQ ID NO: 1, and wherein the two or more amino acid substitutions are selected from the group consisting of (H155V, L200M); (H155G, L200E), (L85H, A125F, H155G, L200M); (A125F, H155G, L200K, L379M); (L200K, L379Q); (A125F, H155T, L200M); (L85H, L200M, L379Q); (L85H, H155G, L200G, L379M); (L85H, A125F, H155V, L200M); (L85H, A125F, H155I, L200C, L379Q); (A125F, L200E, L379Q); (H155T, L200G, L379M); (H155L, L200M); (H155V, L200C); (L85H, H155T, L200G); (L85H, H155I, L200C, L379Q); (H155I, L200M, L379Q); (L85H, A125F, H155T, L200E, L379M); (L85H, H155T, L200M); (H155V, L200C, L379M); (L85H, A125F, L200M, L379M); (H155V, L379Q); (L85H, L200K, L379M); (L85H, A125F, H155L, L200M, L379Q); (L85H, A125F, H155I, L200K, L379M); (H155I, L379M); (L200M, L379M); (L85H, H155V, L200G, L379Q); (H155T, L200E); (H155V, L379M); (A125F, H155I, L379M); (H155V, L200C, L379Q); (L85H, H155G, L200K, L379Q); (A125F, H155G, L200M, L379M); (H155T, L200E, L379Q); (L200K, L379G); (L85H, H155L, L200C, L379M); (A125F, H155I, L200K, L379M); (L85H, H155V, L200M); (L85H, H155V, L200E, L379V); (L85H, H155V, L200M, L379Q); (L85H, L200M, L379M); (H155V, L200E, L379M); (L85H, H155I, L200M, L379M); (L85H, H155I, L200M, L379Q); (L85H, A125F, H155T, L200C, L379M); (L85H, A125F, H155L, L200K, L379M); (V20L, L85M, A125P); (L85H, H155L, L200K, L379M); (L85H, H155V, L200C, L379Q); (H155I, L200K, L379M); (L85H, H155L, L200C); (L85H, A125F, H155L, L379M); (L85H, H155I, L200E, L379M); (L85H, A125F, H155G, L200M, L379M); (L85H, H155L, L200E, L379M); (H155L, L200C); (L85H, H155L, L200C, L379E); (L85H, H155V, L200K, L379Q); (H155T, L200K, L379M); (H155V, L200G, L379M); (L85H, A125F, H155V, L200M, L379M); (A125F, H155G, L200C, L379M); (A125F, H155L, L379M); (L85H, H155L, L200G, L379M); (L85H, H155L, L200E, L379Q); (H155G, L200E, L379M); (H155L, L200C, L379Q); (L85H, H155V, L379M); (L85H, A125F, H155I, L200C, L379M); (H155G, L200C, L379M); (A125F, H155V, L200M, L379M); and (H155L, L200E).

* * * * *